(12) United States Patent
Ellis et al.

(10) Patent No.: US 6,933,469 B2
(45) Date of Patent: Aug. 23, 2005

(54) PERSONAL WARMING SYSTEMS AND APPARATUSES FOR USE IN HOSPITALS AND OTHER SETTINGS, AND ASSOCIATED METHODS OF MANUFACTURE AND USE

(75) Inventors: Kent D. Ellis, Seattle, WA (US); Kenneth S. Siegner, Calimesa, CA (US); Charles C. Wyatt, Corona, CA (US); Jack Wilkerson, Eutis, FL (US)

(73) Assignee: American HealthCare Products, Inc., Redmond, WA (US)

( * ) Notice: Subject to any disclaimer, the term of this patent is extended or adjusted under 35 U.S.C. 154(b) by 0 days.

(21) Appl. No.: 10/419,705

(22) Filed: Apr. 19, 2003

(65) Prior Publication Data

US 2003/0218003 A1 Nov. 27, 2003

Related U.S. Application Data

(63) Continuation-in-part of application No. 09/880,725, filed on Jun. 12, 2001, now Pat. No. 6,653,607.
(60) Provisional application No. 60/457,528, filed on Mar. 24, 2003, and provisional application No. 60/374,853, filed on Apr. 20, 2002.

(51) Int. Cl.$^7$ ................................................ H05B 3/34
(52) U.S. Cl. ........................ 219/217; 219/528; 219/549
(58) Field of Search ................................ 219/212, 217, 219/528, 529, 548, 549, 543; 5/601, 623

(56) References Cited

U.S. PATENT DOCUMENTS

| | | | |
|---|---|---|---|
| 2,255,376 A | 9/1941 | Bull et al. | |
| 2,441,005 A | 5/1948 | Bradford | |
| 2,473,183 A | 6/1949 | Watson | |
| 2,630,288 A | * | 3/1953 | Eubanks, Sr. .................. 5/646 |

(Continued)

FOREIGN PATENT DOCUMENTS

| | | |
|---|---|---|
| CA | 969621 | 6/1975 |
| DE | 2308214 A | 8/1974 |
| DE | 3146234 A1 | 5/1983 |
| DE | 3405425 A | 8/1985 |
| DE | 3707948 A | 9/1988 |
| DE | 3707948 | 9/1988 |

(Continued)

OTHER PUBLICATIONS

Written Opinion, International Application No. PCT/US01/18927, 5 pages.
Partial International Search, International Application No. PCT/US01/18927, Dec. 12, 2001, 2 pages.
International Search Report, International Application No. PCT/US03/12168, Jan. 7, 2004.
International Search Report, International Application No. PCT/US03/28458, Feb. 12, 2004.

*Primary Examiner*—Teresa J. Walberg
(74) *Attorney, Agent, or Firm*—Perkins Coie LLP

(57) ABSTRACT

Personal warming systems and apparatuses for use in hospitals and other settings. In one embodiment, a heating mattress or pad for warming a patient during a hospital procedure can include a heating element positioned between a first foam portion and a second foam portion. The heating element and the foam portions can be at least partially enclosed in a fluid-resistant cover. The heating element can be operably connected to a control unit that allows an operator to select between a plurality of temperature options for the heating pad. In another embodiment, the heating pad can include one or more radiolucent, or at least generally radiolucent, features that will not appreciably obscure x-ray images taken of a patient positioned on the heating pad. In one aspect of this embodiment, the radiolucent features can include one or more of a carbon-based heating element, an optical temperature sensing device, and/or a thermally responsive state-changing device.

23 Claims, 21 Drawing Sheets

U.S. PATENT DOCUMENTS

| | | | |
|---|---|---|---|
| 2,688,070 A | | 8/1954 | Freedlander |
| 3,013,141 A | | 12/1961 | Ellis |
| 3,349,359 A | | 10/1967 | Morey |
| 3,423,574 A | | 1/1969 | Shomphe et al. |
| 3,553,749 A | | 1/1971 | Majeske |
| 3,900,654 A | | 8/1975 | Stinger |
| 4,204,612 A | * | 5/1980 | Schrader et al. ............ 219/421 |
| 4,310,745 A | | 1/1982 | Bender |
| 4,423,308 A | | 12/1983 | Callaway et al. |
| 4,672,176 A | * | 6/1987 | Kishimoto et al. ......... 219/528 |
| 4,788,417 A | | 11/1988 | Graflind |
| 4,833,305 A | | 5/1989 | Mashimo et al. |
| 5,031,261 A | | 7/1991 | Fenner, Sr. |
| 5,136,741 A | | 8/1992 | Balonick et al. |
| 5,138,138 A | * | 8/1992 | Theilacker et al. ......... 219/528 |
| 5,265,296 A | | 11/1993 | Abbas et al. |
| 5,284,701 A | * | 2/1994 | Hamon ........................ 442/73 |
| 5,324,911 A | | 6/1994 | Cranson et al. |
| 5,371,340 A | | 12/1994 | Stanfield |
| 5,385,529 A | | 1/1995 | Koch |
| 5,398,354 A | | 3/1995 | Balonick et al. |
| 5,451,747 A | | 9/1995 | Sullivan et al. |
| 5,494,051 A | | 2/1996 | Schneider, Sr. |
| 5,516,189 A | | 5/1996 | Ligeras |
| 5,604,021 A | | 2/1997 | Wagner |
| 5,720,774 A | | 2/1998 | Glucksman |
| 5,785,716 A | | 7/1998 | Bayron et al. |
| 5,881,410 A | | 3/1999 | Yamada |
| 5,932,129 A | | 8/1999 | Hyatt |
| 5,948,303 A | | 9/1999 | Larson |
| 6,006,136 A | * | 12/1999 | Glucksman ................... 607/98 |
| 6,050,265 A | | 4/2000 | Richardson |
| 6,369,369 B2 | | 4/2002 | Kochman et al. |
| 6,497,951 B1 | | 12/2002 | DeAngelis et al. |
| 6,582,456 B1 | * | 6/2003 | Hand et al. .................. 219/217 |
| 6,658,994 B1 | * | 12/2003 | McMillan .................... 219/386 |
| 2001/0020303 A1 | | 9/2001 | Endo et al. |
| 2001/0022804 A1 | * | 9/2001 | Helmig et al. .............. 374/161 |
| 2002/0019654 A1 | | 2/2002 | Ellis et al. |
| 2002/0117495 A1 | * | 8/2002 | Kochman et al. ........... 219/549 |
| 2002/0133213 A1 | | 9/2002 | Tippitt |
| 2003/0006229 A1 | | 1/2003 | Lin et al. |
| 2003/0178414 A1 | | 9/2003 | DeAngelis et al. |

FOREIGN PATENT DOCUMENTS

| | | |
|---|---|---|
| DE | 29809445 | 8/1998 |
| EP | 677283 A1 | 10/1995 |
| EP | 0 757 907 A1 | 2/1997 |
| GB | 2255262 A | 10/1992 |
| JP | 57-180888 A | 11/1982 |
| JP | 402276185 A | 11/1990 |
| JP | 3-165746 | 7/1991 |
| JP | 03165746 A | 7/1991 |
| JP | 404073883 A | 3/1992 |
| JP | 10-43258 A | 2/1998 |
| JP | 10-43258 | 2/1998 |
| JP | 11214131 A | 8/1999 |
| JP | 2001238924 A | 9/2001 |
| WO | WO01/95841 A2 | 12/2001 |

* cited by examiner

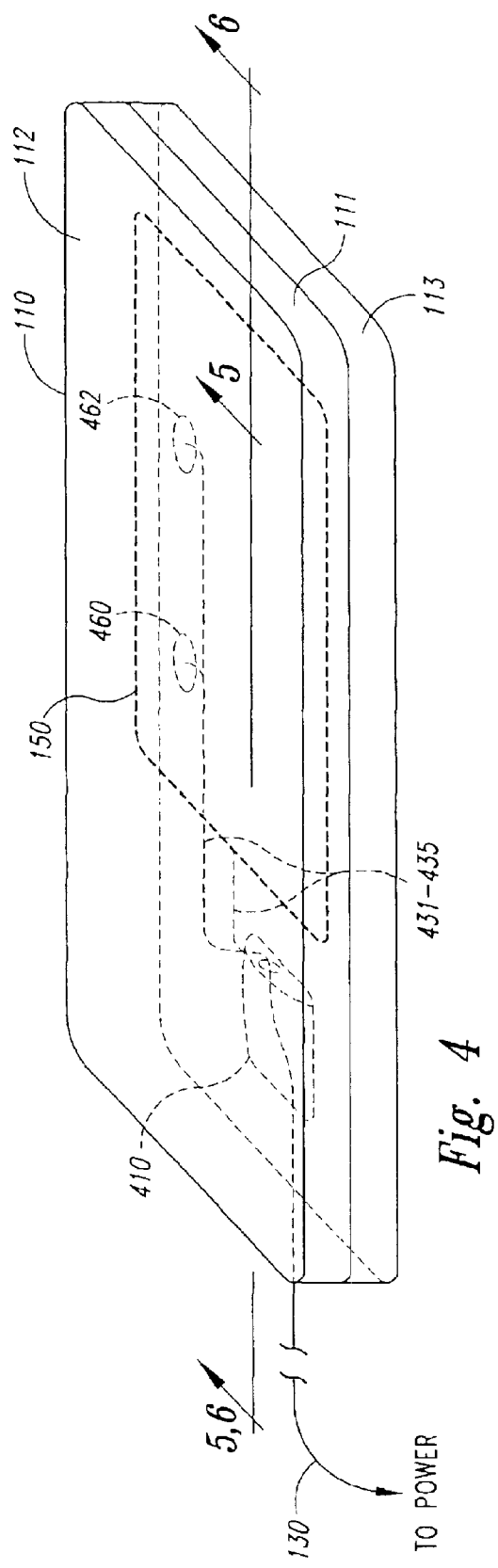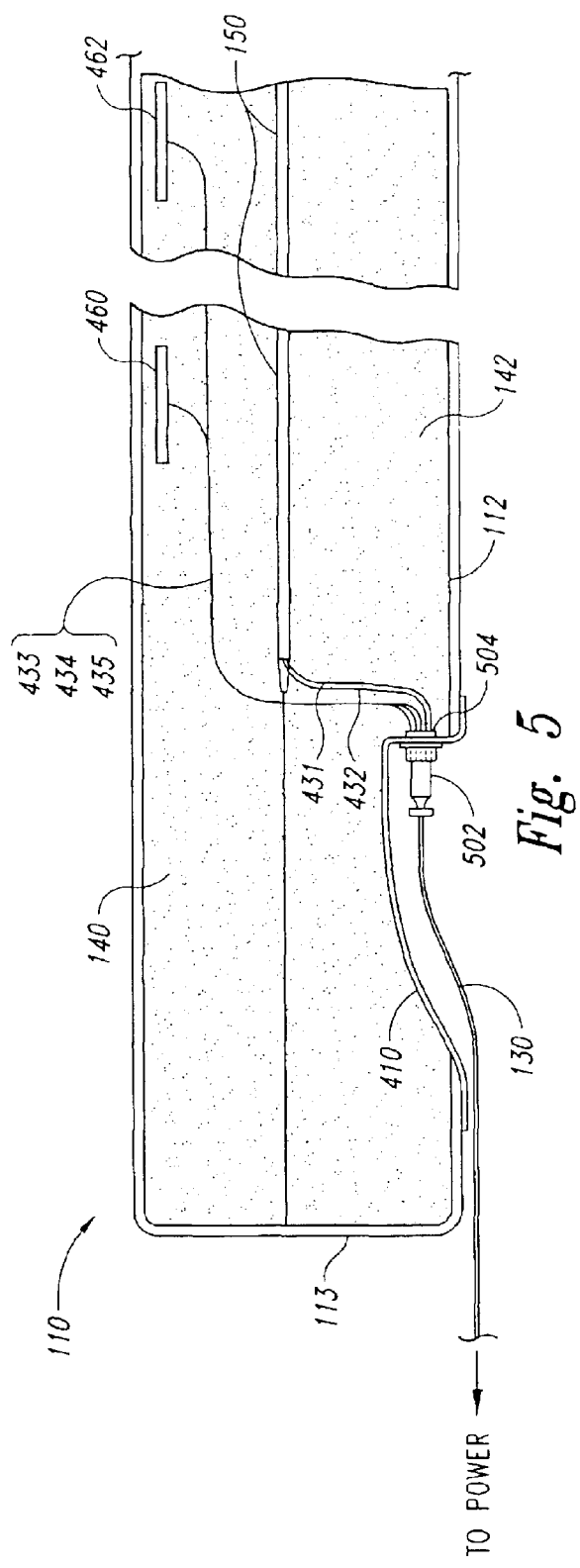
Fig. 4
Fig. 5

PERSONAL WARMING SYSTEMS AND APPARATUSES FOR USE IN HOSPITALS AND OTHER SETTINGS, AND ASSOCIATED METHODS OF MANUFACTURE AND USE

CROSS-REFERENCE TO RELATED APPLICATION(S)

This application is a continuation-in-part of pending U.S. patent application Ser. No. 09/880,725, filed Jun. 12, 2001 now U.S. Pat. No. 6,653,607, which is incorporated herein in its entirety by reference. This application claims the benefit of U.S. Provisional Patent Application No. 60/374,853, filed Apr. 20, 2002, and claims the benefit of U.S. Provisional Patent Application No. 60/457,528, entitled "SYSTEMS AND APPARATUSES FOR WARMING AND POSITIONING PATIENTS," filed Mar. 24, 2003, both of which are incorporated herein in their entireties by reference.

TECHNICAL FIELD

The following disclosure relates generally to personal warming systems and apparatuses and, more particularly, to personal warming systems and apparatuses for warming patients undergoing various hospital procedures.

BACKGROUND

Maintaining patient body temperature at an acceptable level can be very important during some medical procedures because of the significant effect it can have on the outcome of the procedures. If a patient's body temperature is allowed to drop below an acceptable level, the patient could develop hypothermia which can prolong or complicate recovery. If a patient can be kept warm before, during, and after surgery, for example, then post-operative problems such as excessive bleeding, infection, shivering, and cardiac distress can be minimized. Maintaining the patient's body temperature in a surgical setting, however, may be difficult for a number of different reasons. One reason is that the operating room is typically air-conditioned at a relatively cool temperature to maintain air cleanliness and to provide the medical practitioners with a comfortable working environment. Another reason is that many surgical procedures require that at least a portion of the patient be exposed for surgical access. Such surgical access can further accelerate patient cooling if it opens up a large portion of the patient's body, such as the chest cavity. In addition, the onset of hypothermia during certain medical procedures may be accelerated by the patient's body position. For example, elevating the patient's leg to harvest veins for heart surgery may accelerate a decline in the patient's body temperature.

Cardiac catheterization is an invasive procedure in which the doctor threads a catheter through an artery in the patient's arm, groin, neck or leg to the patient's heart. A special dye is introduced into the catheter that allows the doctor to view arterial blockages with an x-ray machine to diagnose the patient's condition. The procedure often requires that a substantial portion of the patient's body be accessible to the doctor for comprehensive x-ray imaging to examine the various blood flows. As a result, much of the patient is exposed or only lightly covered during the procedure, which may cause the patient's body temperature to drop to undesirable levels. For this reason, it may be desirable to warm the patient during the cardiac catheterization procedure to prevent the onset of hypothermia.

Various devices exist for warming patients undergoing medical procedures. One such device pre-warms blankets placed over the patient. Another such device circulates heated air through a sealed blanket placed over the patient. Yet another such device circulates heated water through a sealed blanket placed over the patient.

There are a number of shortcomings associated with existing patient warming devices. The use of pre-warmed blankets, for example, can be expensive because the blankets are often disposed of after each use. Devices utilizing heated air have the additional drawback of circulating high temperature air in close proximity to patients who are often anesthetized. If a hot air duct associated with such a device inadvertently contacted an anesthetized patient, the patient could sustain serious burns before the practitioner or operator noticed the oversight and corrected the situation. In addition, all of these existing patient warming devices generally require high energy inputs to achieve the desired temperatures.

Another shortcoming often associated with existing patient warming devices is that most are configured to inefficiently warm the patient from the top down. This shortcoming often limits use of such devices to those portions of the patient where the medical practitioner does not require access. For example, if the patient is undergoing open heart surgery, then use of such devices would be precluded near the patient's chest. Unfortunately, however, in many surgical procedures the area where the practitioner is operating is often the area most in need of additional warmth.

A further shortcoming often associated with existing patient warming devices is a lack of adequate cleanliness. Body fluids, for example, can often get inside various parts of conventional patient warming devices when such devices are used in a surgical setting. These fluids can present cleanliness concerns for subsequent use of the device. This is one reason why many conventional patient warming devices incorporate disposable components. The use of disposable components, however, can increase the costs of surgical procedures.

Yet another shortcoming often associated with existing patient warming devices is an inability to adequately control the rate or level of patient warming. In certain circumstances, uncontrolled patient warming may complicate the surgical procedure or cause negative side effects in the patient.

BRIEF DESCRIPTION OF THE DRAWINGS

FIG. 4 is a partially hidden top isometric view of a heating pad configured in accordance with an embodiment of the invention.

FIG. 5 is a partial cross-sectional side elevation view of the heating pad of FIG. 4, configured in accordance with an embodiment of the invention.

DETAILED DESCRIPTION

Figure 1:
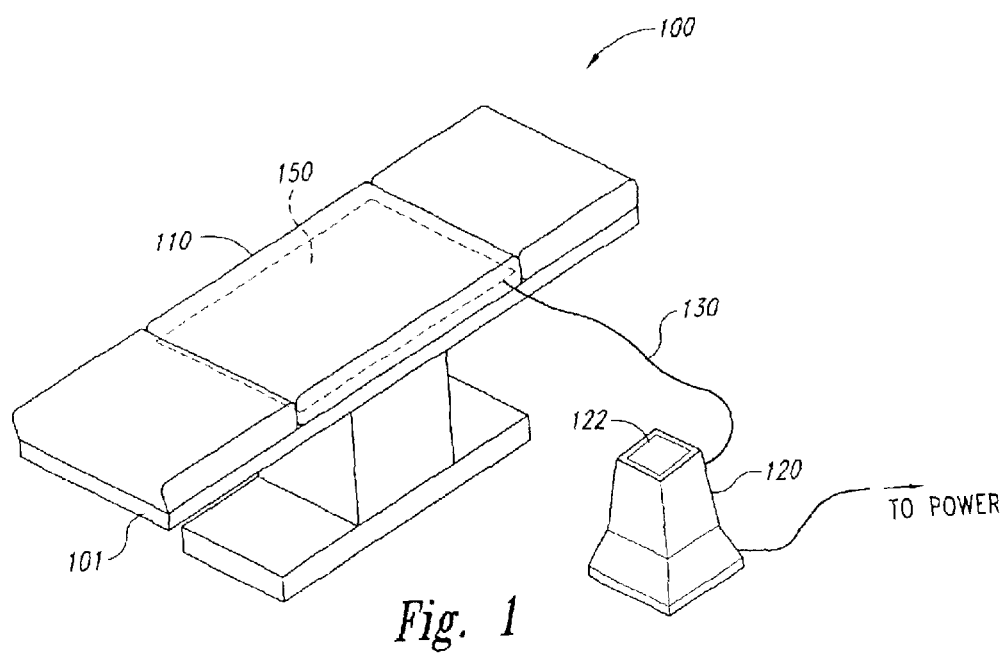
FIG. 1 is a top isometric view of a patient warming system configured in accordance with an embodiment of the invention.

The following disclosure describes various aspects of personal warming systems for use in hospitals and other nonmedical settings. In one embodiment, a patient warming system configured in accordance with the present invention can include a heating pad configured to warm a patient positioned on the pad in a step-wise fashion, allowing the temperature to stabilize at each step before proceeding to the next step. One form of such step-wise warming can include warming the pad from 96.8° F. to 98.6° F. in a first step, warming the pad from 98.6° F. to 100.4° F. in a second step, and warming the pad from 100.4° F. to 102.2° F. in a third and final step. In one aspect of this embodiment discussed in greater detail below, warming the patient in a step-wise fashion may provide certain benefits over warming the patient directly from, for example, 96.8° F. to 102.2° F.

In another embodiment, a patient warming system configured in accordance with the invention can include a heating pad control unit having certain features that facilitate use in hospital operating room (OR) environments. For example, in one aspect of this embodiment, the control unit can include an exterior surface configured to deflect fluids that contact it. In addition, the control unit can have a center of gravity (CG) positioned to stabilize the control unit and prevent it from inadvertently tipping over during use. In a further embodiment, a heating pad control unit configured in accordance with the invention can also include various features for quick and easy attachment to typical OR structures. Such features can include, for example, a releasable clamp for quickly attaching the control unit to an IV pole so that the control unit can be moved around an OR table as needed during an operation. As discussed in greater detail below, many aspects of embodiments of the invention are configured to meet or exceed one or more of the IEC 60601 Standards for Medical Electrical Equipment as set forth by the U.S. Food and Drug Administration Center for Devices and Radiological Health.

In yet another embodiment, a patient warming system configured in accordance with the invention can include one or more heating pads that are at least generally radiolucent. The term radiolucent, as used throughout this disclosure, means that the particular structure is transparent, or at least generally transparent, to x-rays. One advantage of this embodiment is that such heating pads can be used to warm patients during x-ray procedures without obscuring or otherwise preventing acquisition of usable x-ray images. As discussed in greater detail below, such heating pads can include a number of radiolucent features. Such features can include, for example, nonmetallic heating elements, such as carbon ink-based heating elements, fiber optic temperature measurement devices, infrared temperature measurement devices, thermally responsive state-changing devices, such as thermal chromatic devices, and other devices.

In a further embodiment, a patient warming system configured in accordance with the invention can include one or more patient positioning/warming devices. Such positioning/warming devices can include foam structures configured to position a selected portion of the patient in a desired position or orientation to facilitate a medical procedure. In addition to having formed foam structures to position the patient, such devices can also include one or more heating elements configured to generate heat to warm the patient. These and other aspects of the invention are described in detail below.

As used throughout this disclosure, the term "heating pad" will be understood by the reader to include not only pads but mattresses, contoured support structures, and other structures configured to support or otherwise contact a person's body or portions thereof. Additionally, throughout this disclosure, the term "medical procedures" will be understood by the reader to include therapeutic and diagnostic procedures, as well as other types of medical-related activities. Accordingly, references throughout this disclosure to "patients" will be understood by the reader to also include persons undergoing such therapeutic and diagnostic procedures.

Certain specific details are set forth in the following description and in FIGS. 1–22 to provide a thorough understanding of various embodiments of the invention. Other details describing well-known structures and systems are not set forth in the following description, however, to avoid unnecessarily obscuring the description of various embodiments of the invention. The dimensions, angles, and other specifications shown in the following figures are merely illustrative of particular embodiments of the invention. Accordingly, other embodiments can have other dimensions, angles, and specifications without departing from the spirit or scope of the invention. In addition, still other embodiments of the invention can be practiced without several of the details described below.

In the figures, identical reference numbers identify identical or at least generally similar elements. To facilitate the discussion of any particular element, the most significant digit or digits of any reference number refer to the figure in which that element is first introduced. For example, element 110 is first introduced and discussed with reference to FIG. 1.

FIG. 1 is a top isometric view of a patient warming system 100 configured in accordance with an embodiment of the invention. In one aspect of this embodiment, the patient warming system 100 includes a heating pad 110 having a heating element 150 operably connected to a control unit 120 via a utility cord 130. In the illustrated embodiment, the heating pad 110 is positioned on an OR table 101 in a typical OR setting and the control unit 120 is positioned on the floor proximate to the OR table 101. A patient (not shown) can be positioned on top of the heating pad 110 during a particular medical procedure, and the heating pad 110 can provide warmth to the patient to prevent the patient's body temperature from dropping to an undesirably low level during the procedure. In another aspect of this embodiment, the control unit 120 can include a user interface 122 that allows an operator (not shown) to control operation of the heating pad 110. For example, as discussed in greater detail below, the user interface 122 can include one or more temperature selectors that allow the operator to select a pad temperature, and one or more displays for presenting operating information to the operator. Such operating information can include, for example, the pad temperature proximate to the surface of the heating pad 110.

Figure 2:
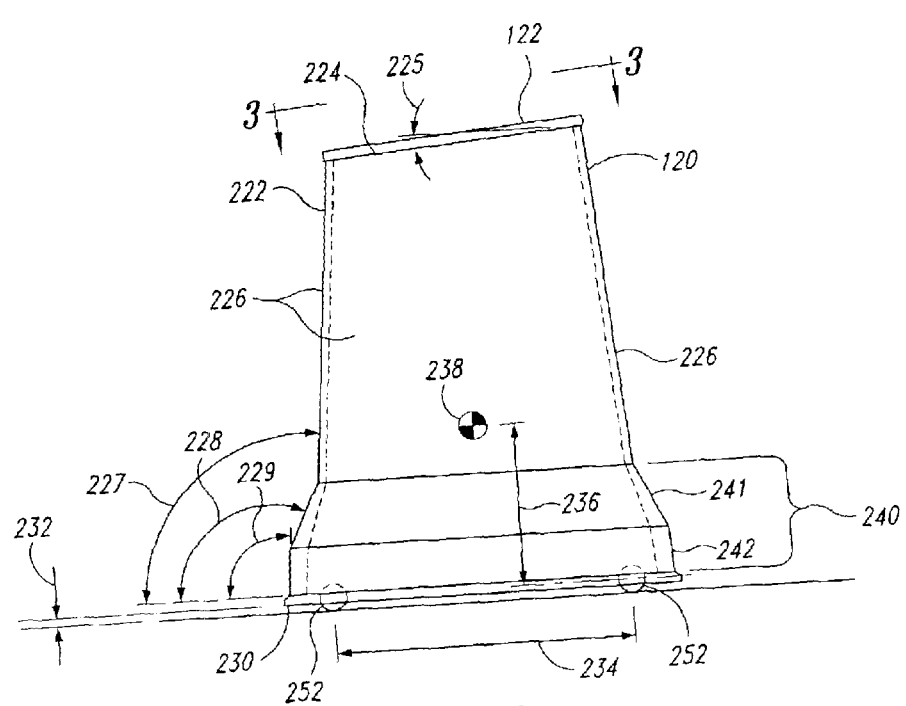
FIG. 2 is a side elevational view of a control unit of the patient warming system of FIG. 1, configured in accordance with an embodiment of the invention.

FIG. 2 is a side elevational view of the control unit 120 of FIG. 1 configured in accordance with an embodiment of the invention. In one aspect of this embodiment, the control unit 120 includes a chassis 222 having an upper portion 224 that supports the user interface 122. The user interface 122 can be sloped at an angle 225 such that fluids or other substances contacting the user interface 122 tend to flow off rather than remain and contaminate or obscure the surface. In one embodiment, the angle 225 can be about 5 degrees. In other embodiments, the angle 225 can have other values. For example, in one other embodiment, the angle 225 can be from about 5 degrees to about 15 degrees. In a further embodiment, the user interface 122 can be at least generally horizontal.

In another aspect of this embodiment, the chassis 222 further includes a plurality of sidewalls 226. In the illustrated embodiment, the sidewalls 226 are canted slightly inboard toward the top portion of the control unit 120 such that fluids and other substances contacting them will flow downwardly and/or outwardly away from the control unit 120. For example, in one embodiment, the sidewalls 226 can be positioned at an angle 227 relative to the horizontal. In one embodiment, the angle 227 can be about 95 degrees. In other embodiments, the sidewalls 226 can be positioned at other angles relative to the horizontal. For example, in one other embodiment, the angle 227 can be from about 95 degrees to about 100 degrees. In another embodiment, the sidewalls 226 can be at least generally vertical.

In a further aspect of this embodiment, the chassis 222 can also include an apron 240 positioned toward the bottom portion of the control unit 120. The apron 240 can include a first angled surface 241 adjacent to a second angled surface 242. Both the first and second angled surfaces 241, 242 can be angled outwardly toward the bottom portion of the control unit 120 to further cause fluids and other substances cascading down the sidewalls 226 to flow off the control unit 120. For example, in one embodiment, the first angled surface 241 can have a first angle 228 of about 114 degrees from the horizontal, and the second angled surface 242 can have a second angle 229 of about 95 degrees from the horizontal. In other embodiments, the first and second angles 228, 229 can have other values. In a further embodiment, the apron 240 can be omitted.

In yet another aspect of this embodiment, the control unit 120 can include a compressible seal 230 extending peripherally around the base portion of the control unit 120. The seal 230 can be configured to restrict or prevent fluids and other substances from moving underneath the control unit 120. In one embodiment, the seal 230 can be positioned a distance 232 of about 0.12 inch above the floor on which the control unit 120 is placed. In other embodiments, the distance 232 can have other values. For example, in one other embodiment, the distance 232 can be from about 0.05 inch to about 1.0 inch. In a further embodiment, the seal 230 can be configured to contact the floor. In yet another embodiment, the seal 230 can be omitted.

In a further aspect of this embodiment, the control unit 120 includes a center of gravity (CG) 238 located a distance 236 above a plurality of rollers 252. In the illustrated embodiment, the rollers 252 can be spaced apart by a distance 234, and the control unit 120 can be configured such that the CG distance 236 is equal to about one-half the distance 234 between the rollers 252. Configuring the control unit 120 in this manner can increase the stability of the control unit 120 to reduce the possibility of it being inadvertently tipped over during use in the OR environment. For example, configuring the control unit 120 in the foregoing manner can result in a control unit that has to be tipped to an angle of at least about 45 degrees before it will tip over. In other embodiments, the control unit 120 can have other configurations without departing from the spirit or scope of the present disclosure. For example, in other embodiments, the rollers 252 can be omitted and the CG 238 can have other locations.

The foregoing description of the control unit 120 is provided here solely to illustrate one embodiment of a control unit configured in accordance with aspects of the present invention. Accordingly, control units configured in accordance with other embodiments of the invention can have features that differ from those described above without departing from the spirit or scope of the present invention.

Figure 3:
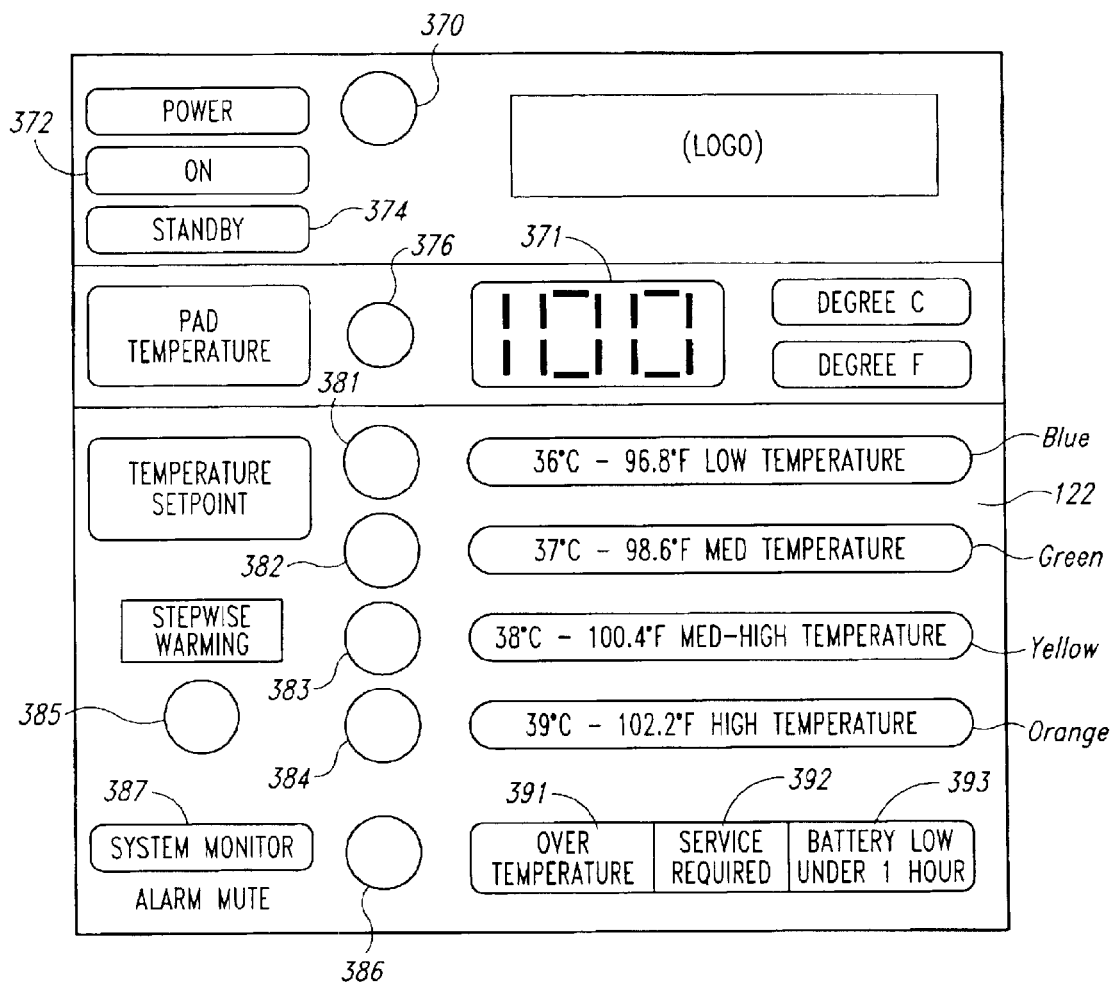
FIG. 3 is a top view of a user interface of the control unit of FIG. 2, configured in accordance with an embodiment of the invention.

FIG. 3 is a top view of the user interface 122 of the control unit 120 taken substantially along line 3—3 in FIG. 2 in accordance with an embodiment of the invention. In one aspect of this embodiment, the user interface 122 includes a standby indicator 374, a power selector 370, and a temperature unit selector 376. When the control unit 120 is operably connected to an electrical source (such as a facility electrical outlet or an internal storage battery) and is switched "on," the standby indicator 374 is illuminated indicating that the control unit 120 is in the "standby" mode. In this mode, an operator can depress the power selector 370 to cause the heating pad 110 (FIG. 1) to start warming up. This action will also cause a power-on indicator 372 to illuminate providing a visual indication that the heating pad is warming. As discussed in greater detail below, the operator can control the temperature of the heating pad 110 with one or more of a plurality of temperature selectors 381–384. As the heating pad temperature rises, the temperature at the surface of the pad is displayed on a temperature display 371. The operator can choose between Centigrade or Fahrenheit temperature units by selectively depressing the temperature unit selector 376.

In another aspect of this embodiment, the temperature selectors 381–384 allow the operator to choose from a range of heating pad temperatures and select the temperature that best suits the particular circumstances. For example, the operator can choose a low temperature of 96.8° F. (selector 381), a medium temperature of 98.6° F. (selector 382), a medium-high temperature of 100.4° F. (selector 383), or a high temperature of 102.2° F. (selector 384). Alternatively, the operator can elect to warm the patient in a step-wise manner using two or more of the temperature selectors 381–384. Step-wise warming of a patient can be accomplished in one embodiment as follows. Initially, the operator can depress the temperature selector 381 causing the surface of the heating pad 110 to warm to a temperature of about 96.8° F. Once the pad's temperature has stabilized at about 96.8° F. (as indicated by the temperature display 371), the operator can depress the temperature selector 382 to warm the heating pad to about 98.6° F. After the pad's temperature has stabilized at about 98.6° F., the operator can depress the temperature selector 383 to warm the pad to about 100.4° F. Step-wise warming of the patient in the foregoing manner may, under certain circumstances, provide certain therapeutic benefits over direct warming of the patient from, for example, a temperature of about 88° F. to about 100.4° F.

Although step-wise patient warming has been described here using a temperature range from about 96.8° F. to about 100.4° F., in other embodiments, the patient may be warmed using other temperature ranges in other manners. For example, in one other embodiment, the patient may be warmed directly from an initial temperature to a selected pad temperature.

In a further aspect of this embodiment, the temperature range fields adjacent to the temperature selectors 381–384 can be different colors to visually and intuitively indicate the associated temperature range. For example, in one embodiment, the "low temperature" field adjacent to the temperature selector 381 can be blue in color to intuitively indicate cooler temperatures less than or equal to about 96.8° F. Similarly, the "medium temperature" field adjacent to the temperature selector 382 can be green in color to intuitively indicate the normal body temperature of about 98.6° F. Further, the "medium-high temperature" field adjacent to the temperature selector 383 can be yellow in color, and the "high temperature" field adjacent to the temperature selector 384 can be orange in color to intuitively indicate temperatures that are somewhat above normal body temperatures.

The present invention is not limited to the particular temperature ranges described above with reference to FIG. 3. Accordingly, in other embodiments, heating devices in accordance with embodiments of the invention can be operated at different temperatures in different ranges without departing from the spirit or scope of the present invention. In addition, in further embodiments the different temperature range options can be omitted and a heating device configured in accordance with the present invention can be operated at a single temperature.

In yet another aspect of this embodiment, the user interface 122 includes a step-wise warming selector 385. The step-wise warming selector 385 can be selected by an operator to automatically implement a step-wise patient warming program. For example, in one embodiment, selecting the step-wise warming selector 385 causes the surface temperature of the heating pad 110 (FIG. 1) to automatically increase from ambient room temperature to about 96.8° F. in a first step, from about 96.8° F. to about 98.6° F. in a second step, and from about 98.6° F. to 100.4° F. in a third step. In one aspect of this embodiment, the heating pad temperature can stabilize at each temperature level for a predetermined period of time before proceeding on to the next temperature level. In a further aspect of this embodiment, the time period at which the heating pad 110 remains at each temperature level can be preselected by the operator. For example, in one embodiment, the operator can choose to have the heating pad 110 maintain each temperature level for a period of about 10 minutes before proceeding to the next level. In other embodiments, the operator can choose other temperatures and other time periods to suit the particular situation.

In a further aspect of this embodiment, the control unit 120 can include one or more alarms to alert the operator if the temperature of the heating pad 110 (FIG. 1) is greater than a selected range or of the system requires attention of some sort. In one embodiment, an audible or visible alarm can activate when the heating pad 110 is operating above the temperature selected by the operator. When such a condition exists, an over temperature indicator 391 on the user interface 122 can illuminate. Similarly, if the heating pad 110 is operating in a low battery condition, then a battery low indicator 393 can illuminate. In one embodiment, the battery low indicator 393 illuminates when there is one hour or less of stored power remaining in the battery. In this situation, the operator can connect the control unit 120 to a suitable electrical outlet to recharge the battery. In another embodiment, an audible or visible alarm can activate when the patient warming system 100 requires service. For example, when such a condition exists, a service required indicator 392 on the user interface 122 can illuminate. In one aspect of this embodiment, illumination of the service required indicator 392 can indicate disconnection of a power cord providing electrical power to the control unit 120.

As described in greater detail below, in one embodiment, the heating pad 110 (FIG. 1) can include two or more temperature sensors configured to determine the temperature proximate to the surface of the heating pad 110. In one aspect of this embodiment, illumination of the service required indicator 392 can also indicate a discrepancy between these two temperature sensors. For example, in one embodiment, if one of the temperature sensors measures a pad temperature that is more than about 5° F. different from the other temperature sensor, then the service required indicator 392 can illuminate to notify the operator of the discrepancy. In response, the operator can investigate the source of the disagreement between the two temperature sensors. In other embodiments, the service required indicator 392 can illuminate under other conditions and for other reasons.

In a further embodiment, the user interface 122 can include an alarm mute selector 386. When selected, the alarm mute selector 386 causes one or more of the alarms described above to be muted. For example, if the control unit 120 includes an audible alarm that activates when the heating pad 110 exceeds a selected temperature, then selecting the alarm mute selector 386 causes the audible alarm to shut off. Similarly, the alarm mute selector 386 can also be depressed to turn off the service required indicator 392. Alternatively, when the alarm mute selector 386 is not selected, a system monitor indicator 387 is illuminated indicating that the patient warming system 100 is being monitored. In other embodiments, the alarm mute selector 386 can be configured differently or it can be omitted.

FIG. 4 is a partially hidden top isometric view of the heating pad 110 of FIG. 1, configured in accordance with an embodiment of the invention. In one aspect of this embodiment, the heating pad 110 includes a cover 112 and a connector housing or pan-down 410 sealably attached to the cover 112. The cover 112 can have a top portion 111 and a bottom portion 113. The top portion 111 can include a cast-coated polyurethane film/polyurethane foam/polyester knit material. For example, in one embodiment, the top portion 111 can include Staftex# COOLH/CPU 150 material as supplied by Stafford Textiles Limited of Lakeshore Blvd. W., Suite 308, Toronto, Ontario, Canada, M8V 1A4. In yet another aspect of this embodiment, the top portion 111 can include such material having a thickness of about 0.08 mm (about 31.5 Mil) and having known antibacterial properties FR to CA 117. In other embodiments, the top portion 111 can include other materials. In yet other embodiments, the bottom portion 113 can also include the foregoing cast-coated polyurethane film/polyurethane foam/polyester knit material.

In another aspect of this embodiment, the pan-down 410 provides a sealed connection between the utility cord 130 and the power and instrumentation lines 431–435 extending from the utility cord 130 to the heating element 150 and temperature sensors 460 and 462 within the heating pad 110. Although the power and instrumentation lines 431–435 are shown in FIG. 4 as extending approximately down the middle of the heating pad 110, in other embodiments, the power and instrumentation lines 431–435 can extend down the sides of the heating pad 110 to improve the radiolucency of the heating pad 110.

FIG. 5 is a partial cross-sectional side elevation view of the heating pad 110 taken substantially along line 5—5 in FIG. 4 in accordance with an embodiment of the invention. In one aspect of this embodiment, the heating pad 110 includes an upper patient support portion or pad 140 and a lower patient support portion or pad 142 at least generally sandwiching the heating element 150. In one embodiment, the pads 140, 142 can include foam materials and compressible foam materials at least generally similar in structure and function to the corresponding foam materials described in detail in U.S. patent application Ser. No. 09/880,725, and U.S. Provisional Patent Application No. 60/374,853. In other embodiments, the pads 140, 142 can include other foam materials. In still further embodiments, the pads 140, 142 (and, indeed, the other foam structures described below) can include other compressible and/or elastic materials that provide pressure relief and/or heat conduction. For example, in one embodiment, the pads 140, 142 can include a fibrous material, such as a nylon fiber. In yet other embodiments, it is expected that the pads 140, 142 can include yet other materials that have pressure relief and heat conducting features similar to some foams. Thus, as will be appreciated by those of ordinary skill in the relevant art, aspects of the present invention are not limited to the use of foam in general or to the use of particular types of foam, but extend to other similar materials that demonstrate characteristics similar to the materials disclosed herein.

The pan-down 410 can be a concave housing sealably attached to the bottom portion 113 of the cover 112, and the lower pad 142 can be contoured adjacent to the pan-down 410 to receive the pan-down 410 flush with the bottom surface of the heating pad 110. Positioning the pan-down 410 beneath the heating pad 110 in this manner can reduce the likelihood of fluids and other substances contaminating the inner portions of the heating pad 110.

A first connector 504 can be mounted to the pan-down 410 and can be connected to power lines 431 and 432 extending to the heating element 150. Similarly, instrumentation lines 433, 434, and 435 can extend from the first connector 504 to the temperature sensors 460 and 462. In one aspect of this embodiment, the temperature sensors 460, 462 can be positioned at least approximately aligned along a centerline of the heating pad 110 so as to be adjacent to a patient's torso when the patient (not shown) is positioned on the heating pad 110. Such positioning can prevent one or both of the temperature sensors 460, 462 from becoming uncovered if the patient lifts a leg or other appendage off the heating pad 110, which could happen if the sensors are positioned laterally across the heating pad 110. In other embodiments, other temperature sensor orientations can be used.

A second connector 502 provided on one end of the utility cord 130 can mate to the first connector 504 to provide electrical connection between the control unit 120 (FIG. 1) and the heating element 150 and the temperature sensors 460 and 462. In one aspect of this embodiment the first connector 504 can be a male connector and the second connector 502 can be a complimentary female connector. Using male connectors on both the heating pad 110 and the control unit 120 avoids having to clean internal connector cavities on these components.

In still other embodiments of heating pads configured in accordance with the invention, the first and second connectors 502, 504 can be omitted and the utility cord 130, or at least a portion of the utility cord 130, can pass directly through the pan-down 410. In these other embodiments, a nut or other sealing collar can attached the utility cord 130 to the pan-down 410 where the utility cord 130 passes through the pan-down 410. In addition, the utility cord 130 can include a pig-tail or other strain relief feature proximate to the pan-down 410 to reduce the likelihood of the utility cord being pulled out of the pan-down 410.

In a further aspect of this embodiment, the cover 112 incorporating the pan-down 410 can be constructed by a method including the following steps: Cut the material to size for the top portion 111 and the bottom portion 113 of the cover 112. Sew two sides and one end of the top and bottom portions 111 and 113 together to form the cover 112 with one open end. Sonic bond the two sewn sides and the one sewn end. Cut out a portion of the bottom portion 113 to accept the pan-down 410. Glue the periphery of the pan-down 410 to the bottom portion 113 of the cover 112. Install the internal components of the heating pad 110 (e.g., the upper and lower pads 140 and 142, the heating element 150, etc.) and connect the power and instrumentation lines 431–435 between the first connector 504 and the heating element 150 and the temperature sensors 460, 462. Relieve the lower pad 142 to receive the pan-down 410 to ensure a flat profile at the bottom surface of the heating pad 110. Once all electrical connections have been verified and the electrical components in the heating pad 110 have been verified as operational, sew the last end (head end) of the cover 112 together. To ensure a waterproof seal, apply water barrier tape directly over sewn head end seam. Optionally use a heat gun to facilitate adhesion of the water barrier tape. In other embodiments, other methods for constructing the cover 112 can be used. For example, in one other embodiment, the cover 112 can include a fluid-resistant zipper (not shown in FIG. 5) that allows the cover 112 to be removed and replaced if contaminated or damaged.

Figure 6:
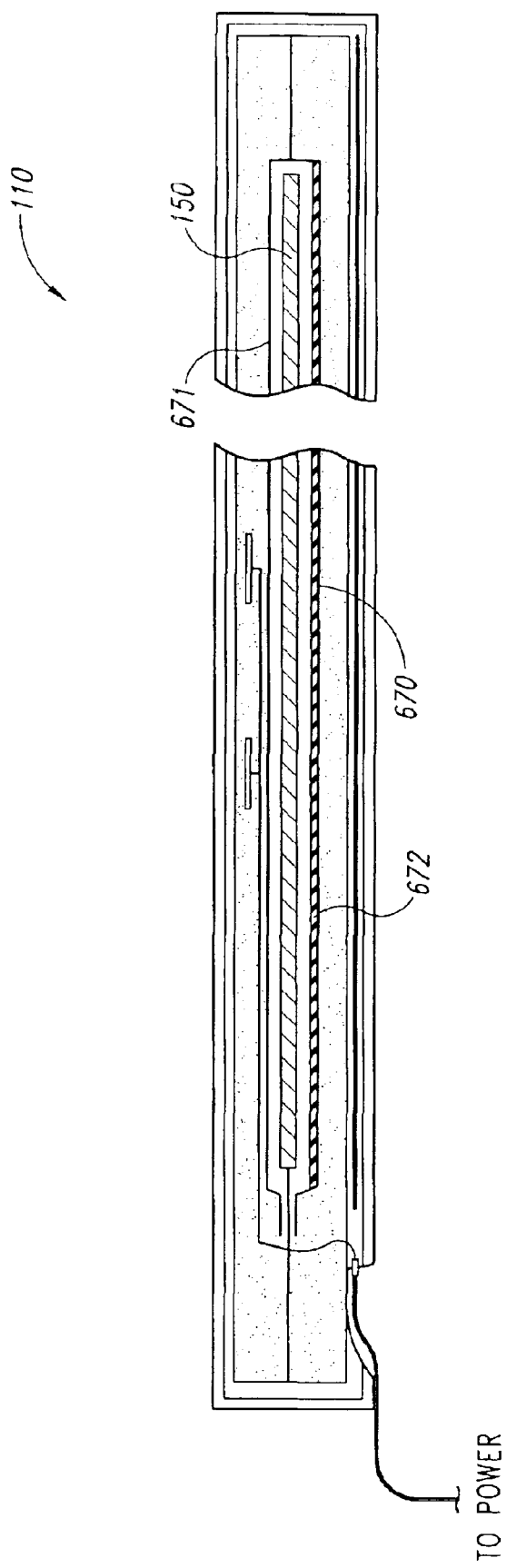
FIG. 6 is a foreshortened cross-sectional side elevation view of the heating pad of FIG. 4, configured in accordance with an embodiment of the invention.

FIG. 6 is a cross-sectional side elevation view of the heating pad 110 taken substantially along line 6—6 in FIG. 4. In one aspect of this embodiment, the heating pad 110 includes a sleeve 670 at least partially enclosing the heating element 150. The sleeve 670 can include a carbon-fiber material such as Kevlar®. In other embodiments, the sleeve can include other materials. In a further aspect of this embodiment, the sleeve 670 can have a bottom portion 672 and a top portion 671. The bottom portion 672 can include a woven fiberglass fabric laminated to the sleeve 670 adjacent to the heating element 150. In other embodiments, the woven fiberglass fabric can be omitted.

In another aspect of this embodiment, the heating element 150 can include a Mylar® polyester material with a copper foil bus embedded in conductive silver ink. For example, in one embodiment, the heating element 150 can include a DuPont Mylar® polyester that is 0.016 inch thick and has 70 micron-thick copper foil embedded in conductive carbon ink (or, alternatively, silver ink). In this embodiment, the heating element 150 can utilize 24 volt power at 50 watts. Flexel International Ltd. of Queensway Industrial Estate, Glenrothes, Fife, Scotland, KY7 5QF is one source for portions of the heating element 150 configured in accordance with this embodiment. For example, in one embodiment, the heating element 150 can include Mark IV type F heating element material offered by Flexel. In other embodiments, other materials can be used for the heating element 150.

Figure 7:
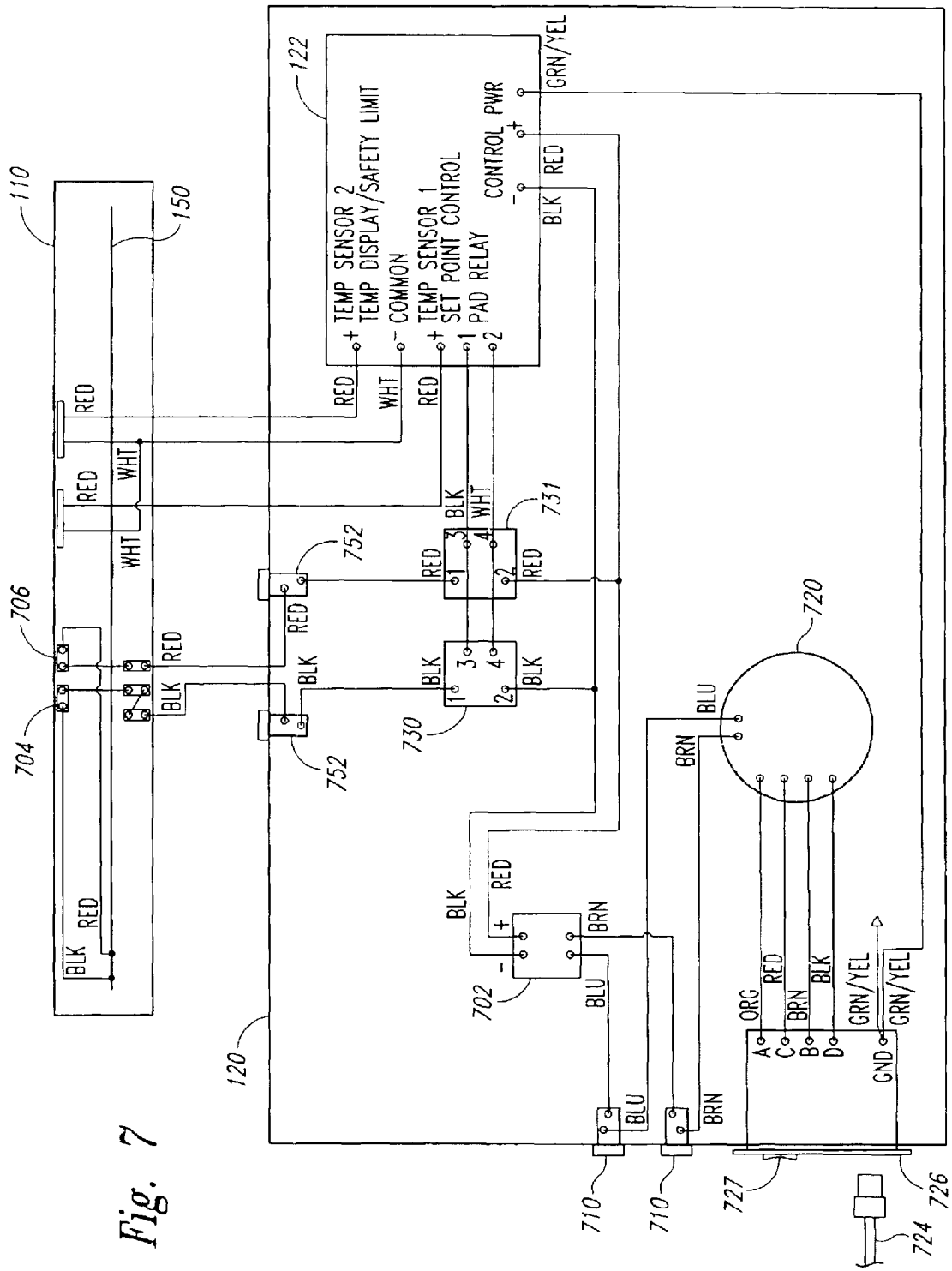
FIG. 7 is a schematic diagram of the control unit and the heating pad of FIG. 1, configured in accordance with an embodiment of the invention.

FIG. 7 is a schematic diagram of the control unit 120 and the heating pad 110 of FIG. 1 configured in accordance with an embodiment of the invention. In one aspect of this embodiment, the control unit 120 can include a connector receptacle 726, fuse holders 710, a transformer 720, a rectifier 702, pad relays 730 and 731, and the user interface 122. A retractable power cord 724 can be received in the receptacle 726 to introduce electrical power to the control unit 120. The receptacle 726 can include a voltage selector 727 that, in one embodiment, allows an operator to select between 115 volts and 230 volts. In one embodiment, the transformer 720 converts standard AC voltage from a hospital facility outlet to 24 volts DC. Power from the transformer 720 can proceed via the fuse holders 710, the rectifier 702, and the pad relays 730 and 731 to the heating element 150 in the heating pad 110. In one aspect of this embodiment, in-line fuses 752 can be employed to avoid electrically overloading the circuit.

In one embodiment, the patient warming system shown schematically in FIG. 7 can be at least generally similar in structure and function to the heating pad system described in pending U.S. patent application Ser. No. 09/880,725. In one aspect of this embodiment, however, the heating pad 110 can include thermostats 704 and 706 that prevent the heating pad 110 from exceeding a surface temperature of 41° C. In other embodiments, the thermostats 704 and 706 can be set at other temperatures or they can be omitted. In yet another embodiment, activation of the thermostats 704 and 706 can cause the over temperature indicator 391 shown in FIG. 3 to illuminate.

Figure 8:
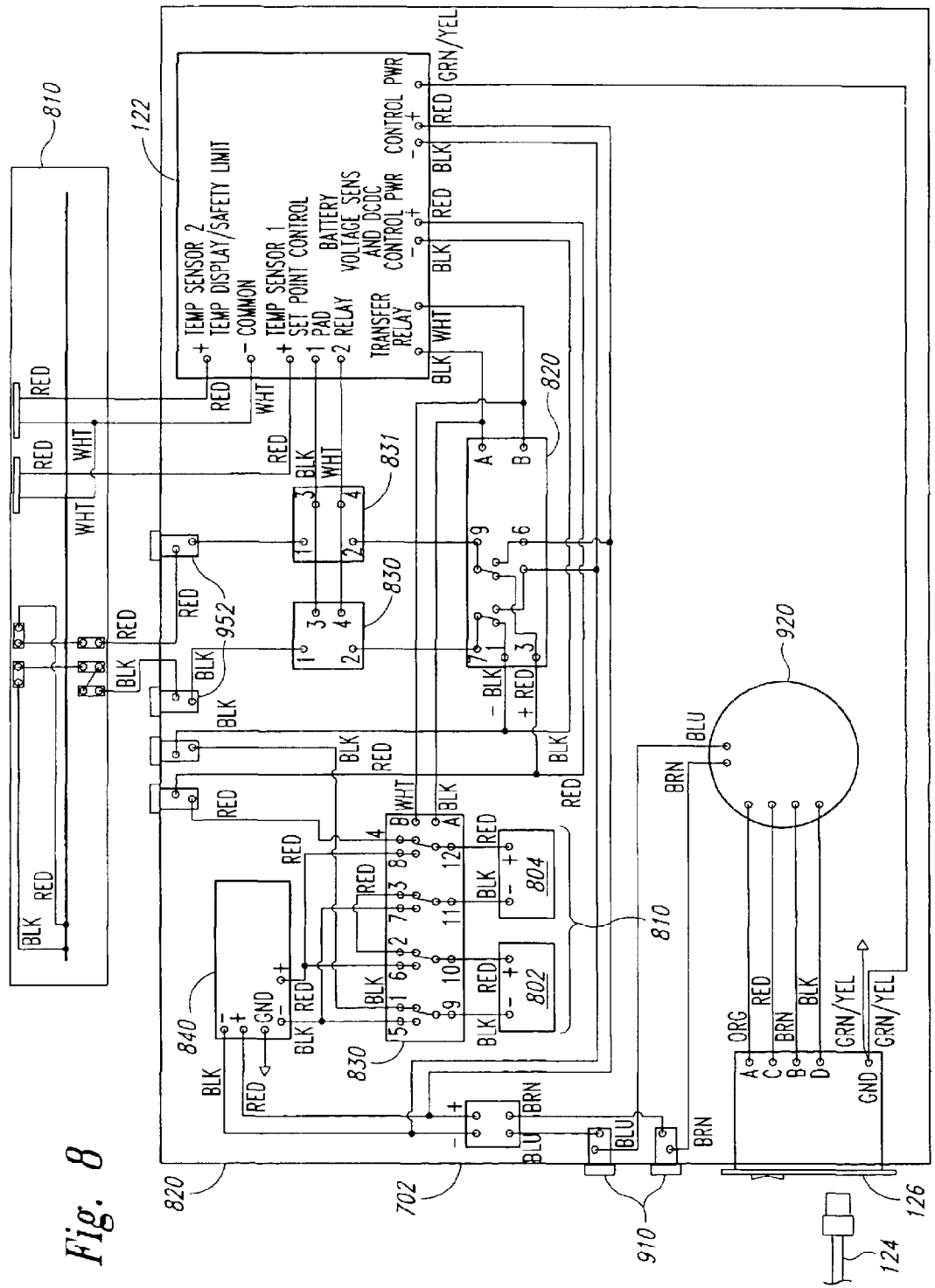
FIG. 8 is a schematic diagram of a control unit and a heating pad configured in accordance with another embodiment of the invention.

FIG. 8 is a schematic diagram of a control unit 820 and a heating pad 810 configured in accordance with another embodiment of the invention. In one aspect of this embodiment, the heating pad 810 and the control unit 820 can be portions of a gurney heating pad system. In another aspect of this embodiment, components of the control unit 820 can be substantially similar to corresponding components of the control unit 120 described above with reference to FIG. 7. Further, certain aspects of the control unit 820 and the heating pad 810 can be substantially similar to the power unit 220 and heating pad 210, respectively, described in pending U.S. patent application Ser. No. 09/880,725. In one aspect of this embodiment, however, the control unit 820 can include an internal power source 810 having batteries 802 and 804. In one embodiment, the batteries 802 and 804 can include 12 amp-hour/12 VDC batteries, such as Panasonic LC-R1212P batteries. In other embodiments, other power storage devices can be used.

The internal power source 810 can enable the heating pad 810 to function independently of an external power source, allowing the heating pad 810 to be moved outside the range of fixed electrical outlets. The internal power source 810 is connected to a charge relay 830 and a charge controller 840. When the control unit 820 is connected to an external power source (such as a facility electrical outlet) via a power cord 824, power from the outside source flows to the batteries 802 and 804 via the charge controller 840 and the charge relay 830 to recharge the batteries 802 and 804 if need be. In addition, power from the outside power source flows to a transfer relay 820 and from there to the heating pad 810 via pad relays 830 and 831. If, however, the control unit 820 is not connected to an external power source, then the charge relay 830 directs power from the batteries 802 and 804 to the heating pad 810 via the transfer relay 820 and the pad relays 830 and 831. Accordingly, in this manner, the heating pad 810 can use an external power source when available and automatically switch to the internal power source 810 when external power is not available.

Figure 9:
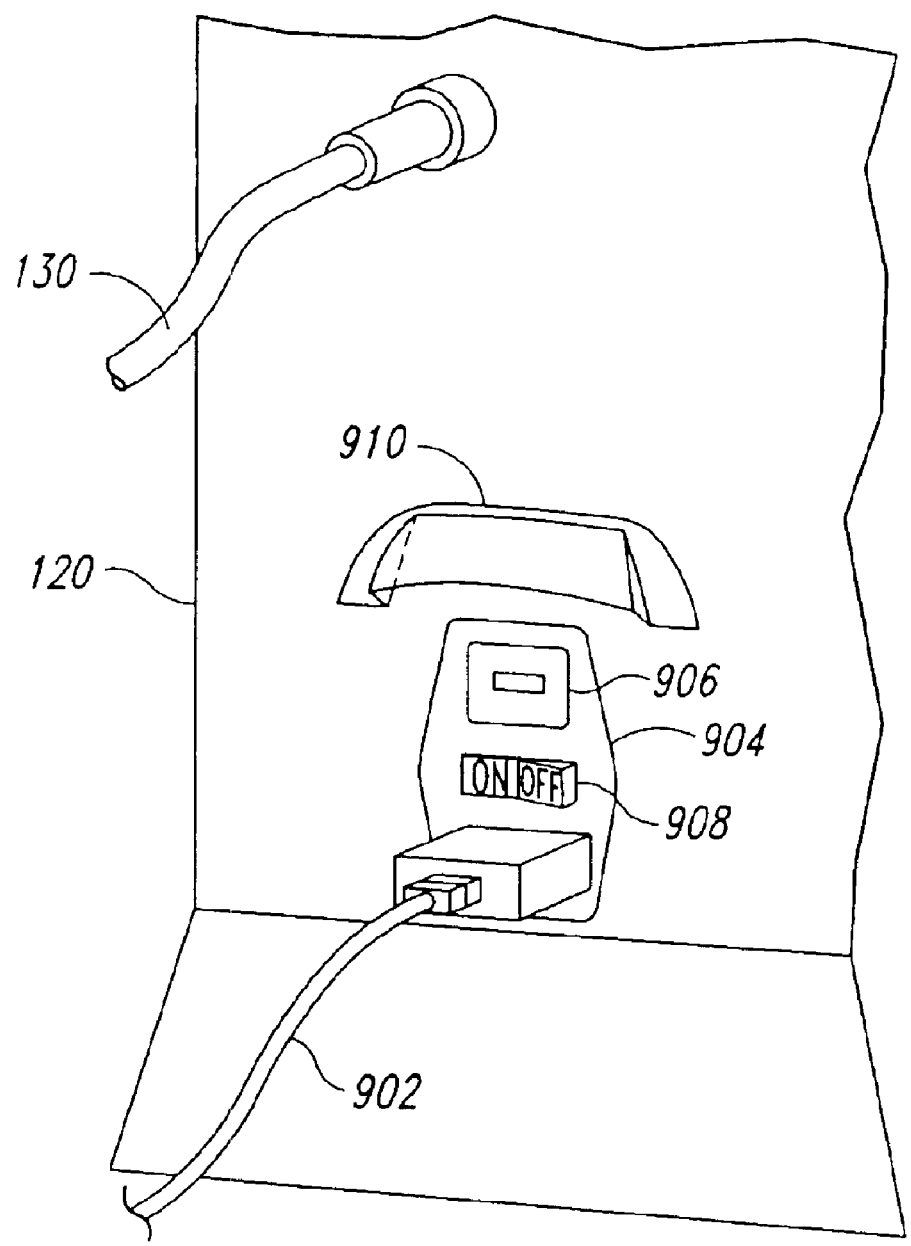
FIG. 9 is an enlarged partial cut-away isometric view of a portion of the control unit of FIG. 1 illustrating a connector shield configured in accordance with an embodiment of the invention.

FIG. 9 is an enlarged, partial cut away isometric view of the control unit 120 of FIG. 1 configured in accordance with an embodiment of the invention. In one aspect of this embodiment, the control unit 120 includes a connector 904 that receives an external power cord 902. A distal end (not shown) of the power cord 902 can be connected to an external power source, such as a facility electrical outlet, to provide electrical power to the control unit 120. In a further aspect of this embodiment, the connector 904 includes a fuse holder 906 and an on/off switch 908. Once the power cord 902 has been connected to a suitable power outlet, the control unit 120 can be powered up by switching the on/off switch 908 to the "on" position. If the control unit 120 is being used with 115V external power (typical in the U.S.A.), then the fuse holder 906 can be configured to accommodate 115V power by orienting the fuse holder 906 in a first position in its receptacle. Conversely, if the control unit 120 is being used with 220V power (typical in Europe), then the fuse holder 906 can be configured to accommodate 220V by rotating the fuse holder 180 degrees from the 115V first position. In yet another aspect of this embodiment, the control unit 120 includes a shield 910 positioned above the connector 904 to deflect fluids or other substances away from the connector 904 to prevent fluid ingress into the control unit 120.

Figure 10:
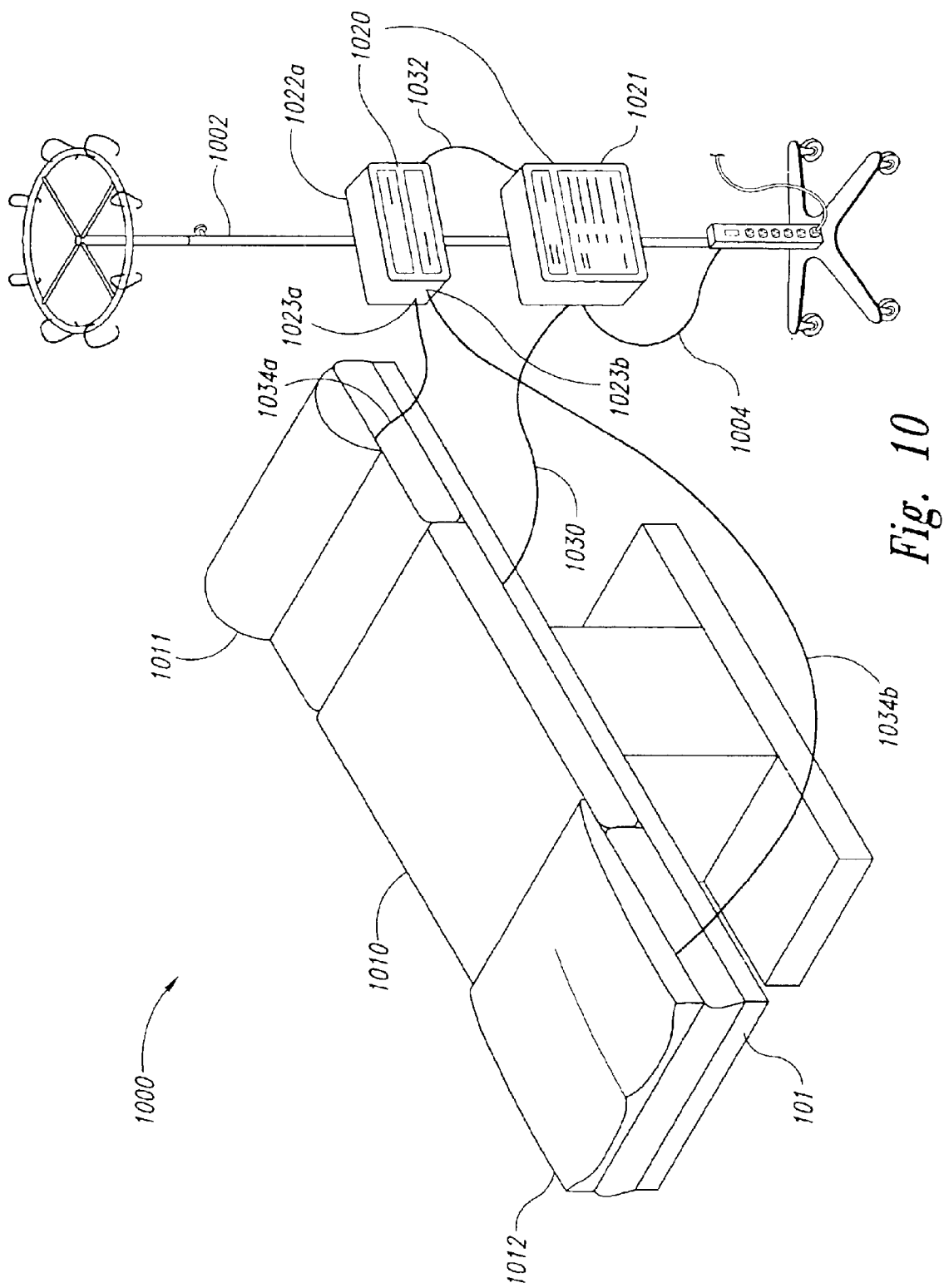
FIG. 10 is a top isometric view of a patient warming system configured in accordance with another embodiment of the invention.

FIG. 10 is a top isometric view of a patient warming system 1000 that includes a number of patient warming devices configured in accordance with an embodiment of the invention. In one aspect of this embodiment, the patient warming system 1000 includes a control system 1020 configured to be carried by a typical OR structure such as an IV pole 1002. The IV pole 1002 can provide mobility to the control system 1020 to facilitate movement of the control system 1020 about the OR. Although the main control unit 1021 and the accessory control unit 1022a of the illustrated embodiment are attached to the IV pole 1002, these control units are further configured to attach to other structures. For example, such other structures can include tech stands, OR tables, beds, cribs or bassinets. This flexibility in attachment offers versatility for use of these respective control units and the associated heating pads in an OR, a PACU, a burn unit, or a neonatal care unit.

In the illustrated embodiment, the control system 1020 includes a first or main control unit 1021 and a second or accessory control unit 1022a. The main control unit 1021 can be at least generally similar in structure and function to the control unit 120 described above with reference to FIGS. 1–9. Further, the main control unit 1021 can also be at least generally similar in structure and function to one or more of the control units described in pending U.S. patent application Ser. No. 09/880,725, or in pending U.S. Provisional Patent Application No. 60/374,853.

The main control unit 1021 can receive standard AC power from a hospital electrical outlet or other source via a power cord 1004. The main control unit 1021 can in turn provide power and control signals to a heating pad 1010 positioned on the OR table 101 via a utility cord 1030. In a further aspect of this embodiment, the heating pad 1010 can be at least generally similar in structure and function to the heating pad 110 described above with reference to FIGS. 1–9. In other embodiments as described below, however, the heating pad 1010 may differ from the heating pad 110.

In addition to providing power and control signals to the heating pad 1010, the main control unit 1021 can also provide power to the accessory control unit 1022a via an accessory cable 1032. The accessory control unit 1022a can include a plurality of outlets 1023a, b for providing power to one or more additional patient warming devices. For example, in the illustrated embodiment, the accessory control unit 1022a provides power to a first patient warming device 1011 via a first cable 1034a, and to a second patient warming device 1012 via a second cable 1034b. As explained in greater detail below, the patient warming devices 1011 and 1012 can include one or more foam portions at least partially enclosing heating elements that receive power via the cables 1034a, b. In addition to providing warmth to the patient, the warming devices 1011 and 1012 can also be shaped and sized to position the patient in selected orientations to facilitate various types of medical procedures. This feature can enable a practitioner to position a patient in such a way as to facilitate a particular medical procedure without compromising the patient's body temperature.

The patient warming system 1000 can include a number of features to enhance its versatility in an OR environment. In one embodiment, for example, each of the different patient warming devices 1010, 1011, and 1012 can be set to a different temperature if desired by the medical practitioner to, for example, facilitate a particular procedure or induce a particular therapeutic effect. In other embodiments, each of the patient warming devices can be set to the same temperature. Thus, various portions of the patient's body can be maintained at different temperatures or the same temperature depending on the particular application.

Figure 11A:
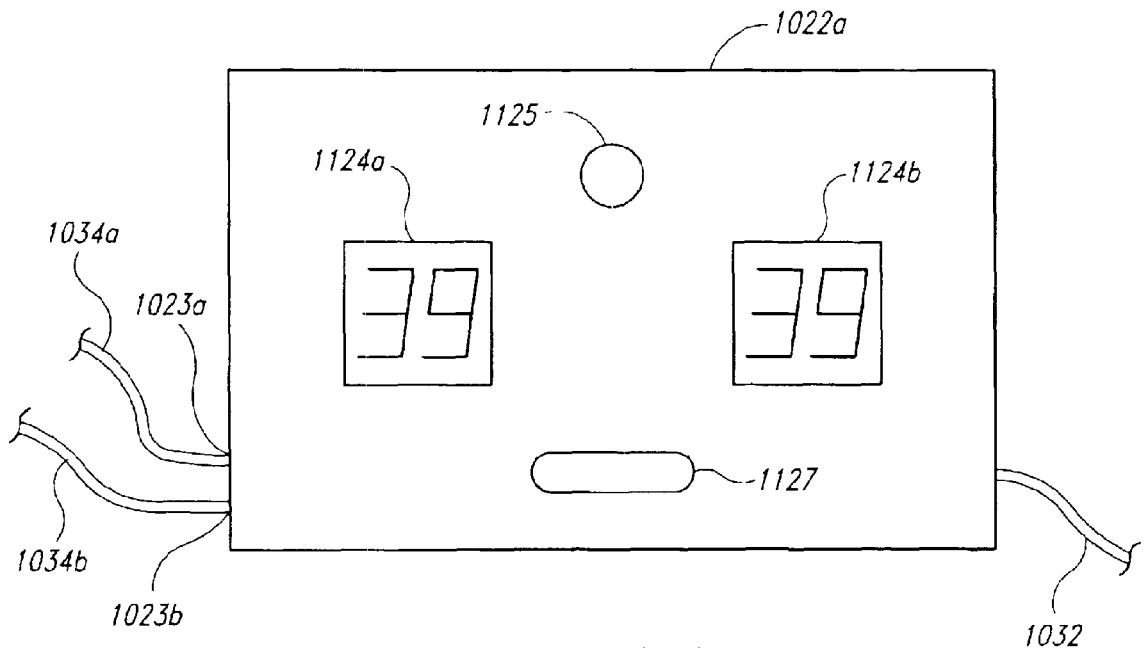
FIG. 11A is an enlarged front view of an accessory control unit configured in accordance with an embodiment of the invention.
Figure 11B:
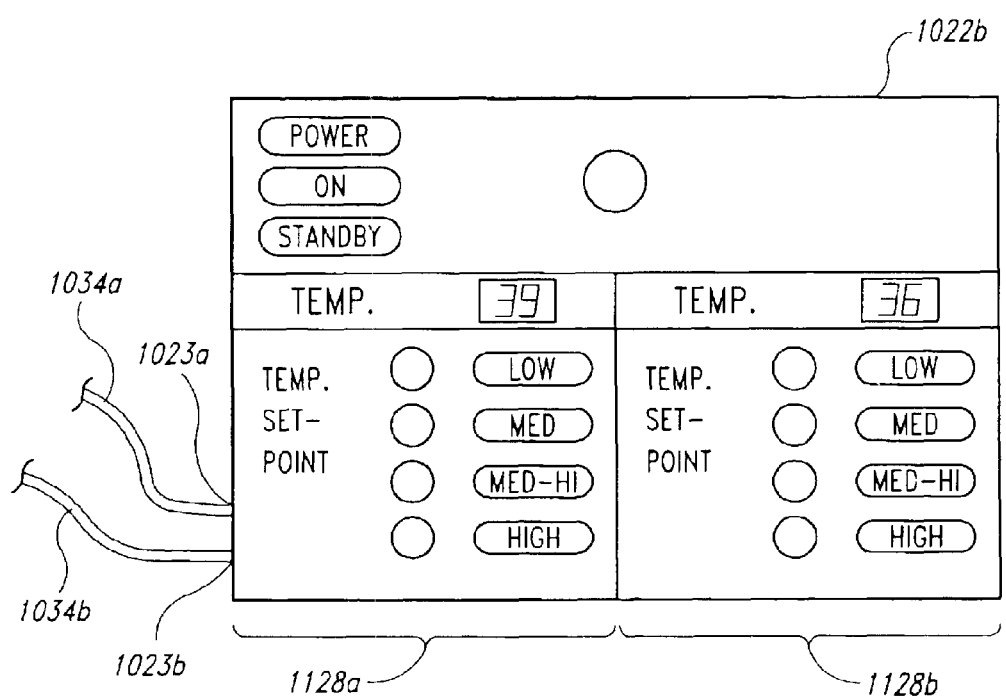
FIG. 11B is an enlarged front view of an accessory control unit configured in accordance with another embodiment of the invention.

FIG. 11A is an enlarged front view of the accessory control unit 1022a of FIG. 10 configured in accordance with an embodiment of the invention, and FIG. 11B is an enlarged front view of an accessory control unit 1022b configured in accordance with another embodiment of the invention. Referring first to FIG. 11A, in one aspect of this embodiment, the accessory control unit 1022a includes a first temperature display 1124a and a second temperature display 1124b. The first temperature display 1124a can be configured to display a temperature of the patient warming device 1011 (FIG. 10) connected to the accessory control unit 1022a via the first cable 1034a. Similarly, the second temperature display 1124b can be configured to display a temperature of the patient warming device 1012 (FIG. 10) connected to the accessory control unit 1022a via the second cable 1034b. In another aspect of this embodiment, the accessory control unit 1022a may not include separate temperature selectors for independently controlling the temperatures of the patient warming devices 1011 and 1012. Accordingly, in this embodiment, an operator can select temperatures for the patient warming devices 1011 and 1012 with the main control unit 1021 of FIG. 10 as described above, for example, with reference to FIG. 3. As a result, in this embodiment, each of the patient warming devices 1010, 1011, and 1012 is controlled at the same temperature by the main control unit 1021.

In a further aspect of this embodiment, the accessory control unit 1022a can also include a power selector 1125 and a warning indicator 1127. The power selector 1125 can be used to turn the accessory control unit 1022a on and off. In other embodiments, the power selector 1125 can be omitted and the accessory control unit 1022a may become active immediately upon connection to the control system 1020. In one embodiment, the warning indicator 1127 can be a light that is illuminated if the temperature of one or more of the patient warming devices 1010, 1011 and 1012 exceeds the selected temperature. In other embodiments, the warning indicator 1127 can be omitted.

Referring now to FIG. 11B, in one aspect of this embodiment, the accessory control unit 1022b includes a first control set 1128a for independently controlling the temperature of a first patient warming device, and a second control set 1128b for independently controlling the temperature of a second patient warming device. In one aspect of this embodiment, one or more of the features of the accessory control unit 1022b can be at least generally similar in structure and function to corresponding features of the user interface 122 described above with reference to FIG. 3. Further, one or more of the features of the accessory control unit 1022b can also be at least generally similar in structure and function to corresponding features of the control units described in pending U.S. patent application Ser. No. 09/880,725, or in pending U.S. Provisional Patent Application No. 60/374,853. For example, the control sets 1128 can each include a temperature display and a plurality of temperature selectors. The temperature selectors can include a low temperature selector (e.g., 96.8° F.), a medium temperature selector (e.g., 98.6° F.), medium-high temperature selector (e.g., 100.4° F.), and a high temperature selector (e.g., 102.2° F.). In other embodiments, the control sets 1128 can include other temperature options.

Although the accessory control units 1022a, b described above are configured to accommodate two patient warming devices via the outlets 1023a, in other embodiments, accessory control units in accordance with the present invention can accommodate more or fewer patient warming devices without departing from the spirit or scope of the present invention. For example, in another embodiment, an accessory control unit configured in accordance with the present invention can accommodate four or more patient warming devices for use with multiple OR tables. In a further embodiment, such an accessory control unit may accommodate only a single patient warming device. Thus, accessory control units configured in accordance with the present invention for controlling patient warming devices and, more specifically, for controlling patient warming and positioning devices, are not limited to the particular embodiments described herein.

Figure 12:
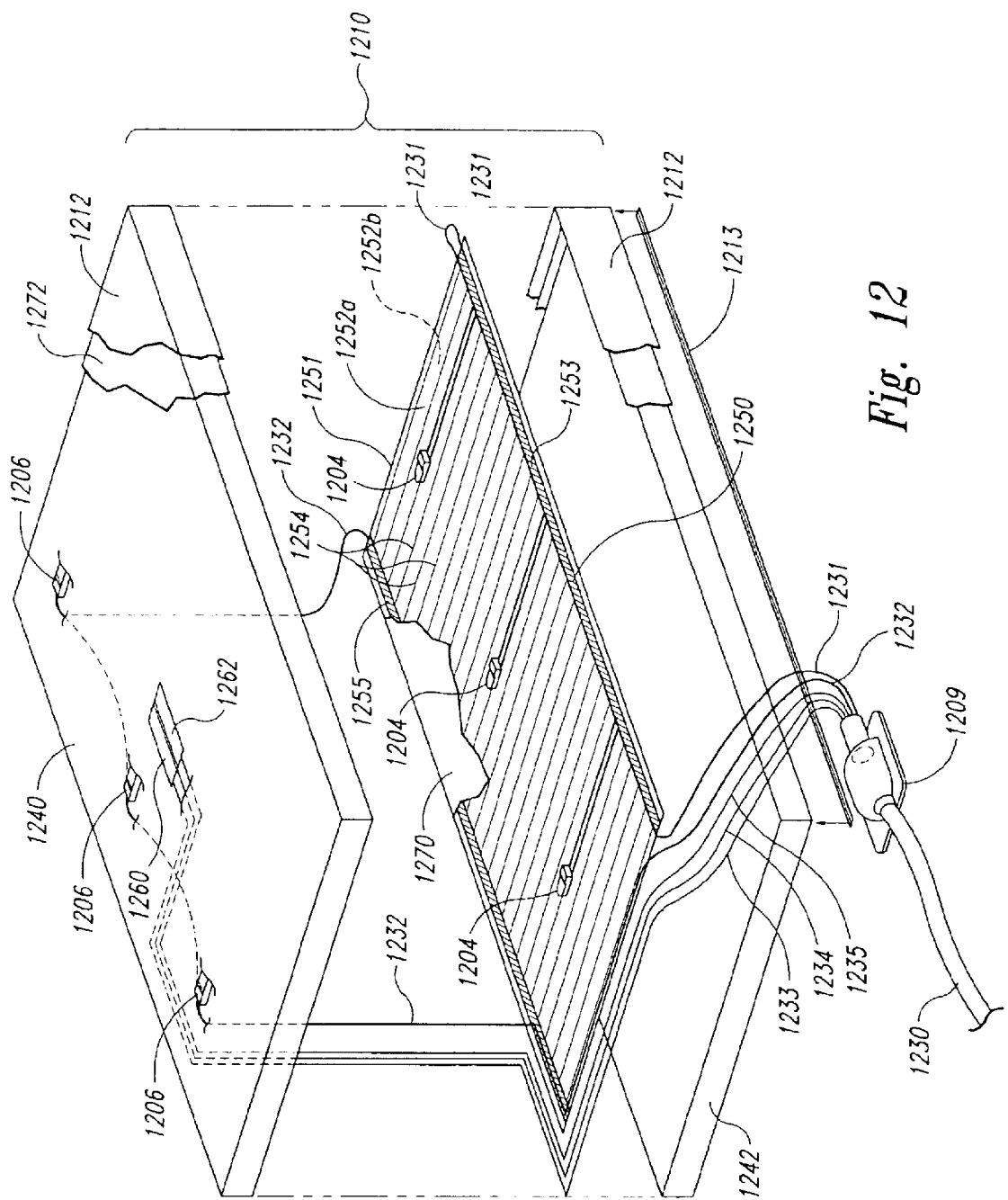
FIG. 12 is an exploded, partially hidden, partially cut away top isometric view of a heating pad configured in accordance with another embodiment of the invention.

FIG. 12 is an exploded, partially hidden, partially cut away top isometric view of a heating pad 1210 configured in accordance with another embodiment of the invention. In one aspect of this embodiment, the heating pad 1210 includes a heating element 1250 positioned at least generally between a first foam portion 1240 and a second foam portion 1242. The first foam portion 1240 can include a viscoelastic foam having a thickness of about 1 inch. In other embodiments, the first foam portion 1240 can include other types of foam having other thicknesses. In another aspect of this embodiment, the second foam portion 1242 can include a high-density polyurethane foam having a thickness of about 2.5 inches. In other embodiments, the second foam portion 1242 can include other types of foam having other thicknesses.

In a further aspect of this embodiment, the heating element 1250 can include a first bus bar or first lead 1253 and a second bus bar or second lead 1255 positioned along opposite edges of a flexible support member 1251. In the illustrated embodiment, the flexible support member 1251 includes a first film layer 1252a and a second film layer 1252b. In one embodiment, the film layers 1252 can include a polyester film. In other embodiments, the film layers 1252 can include other materials. In another aspect of this embodiment, the first and second leads 1253, 1255 can include copper material. For example, in one embodiment, the first and second leads 1253, 1255 can include braided copper, braided silver, or other metallic and non-metallic conductive materials.

In yet another aspect of this embodiment, the heating element 1250 can further include electrically conductive carbon ink portions 1254 extending between the first lead 1253 and the second lead 1255. Accordingly, when each of the leads 1253, 1255 is biased at a different electrical potential, the carbon ink portions 1254 can conduct electrical current across the heating element 1250 to generate heat for warming the heating pad 1210. One advantage of using carbon ink in this manner is that it is at least generally radiolucent. As a result, it will not obscure or otherwise impair x-ray images taken of a patient positioned on the heating pad 1210.

In a further aspect of this embodiment, the heating element 1250 or portions thereof can be provided by Flexel International, Ltd. Corporation of Scotland. In other embodiments, the heating element 1250 or portions thereof can include a silver oxide conductive material provided by Green Textiles, Inc. of South Carolina, U.S.A. In yet another embodiment, the heating element 1250 or portions thereof can include Gorix material from England. In still further embodiments, the heating element 1250 can include materials and components in different configurations and from different sources without departing from the spirit or scope of the present disclosure. For example, in another embodiment, it is expected that the heating element 1250 can include carbon strands woven in a cloth substrate, such as GVP material from Italy.

In another aspect of this embodiment, the heating pad 1210 can include a connector housing or pan-down 1209 configured to introduce power and/or instrumentation lines from a utility cord 1230 into the heating pad 1210. As discussed in greater detail below, the heating pad 1210 can also include a form-fitting and fluid-resistant cover 1212 to which the pan-down 1209 is sealably attached. Further, the second foam portion 1242 can be recessed or locally contoured to receive the pan-down 1209 in such a way that the heating pad 1210 will sit at least generally flat on an OR table or other supporting surface.

Power lines 1231, 1232 pass from the utility cord 1230 into the heating pad 1210 via the pan-down 1209. In a further aspect of this embodiment, the first power line 1231 can be operatively connected to the first lead 1253 and can be configured to bias the first lead 1253 at +24 VDC. Similarly, the second power line 1232 can be operatively connected to the second lead 1255 and can be configured to bias the second lead 1255 at −24 VDC. Accordingly, when the utility cord 1230 is connected to a suitable power source (such as the main control unit 1021 described above with reference to FIG. 10), the power lines 1231 and 1232 bias the respective leads 1253, 1255 at different potentials causing current to flow between the leads 1253, 1255 via the carbon ink portions 1254.

Instrumentation lines 1233, 1234, and 1235 extend from the pan-down 1209 through adjacent portions of foam to a first temperature sensor 1260 and a second temperature sensor 1262. The first and second temperature sensors 1260, 1262 can be configured to sense the temperature proximate to the top surface of the first foam portion 1240. As described above, the sensed temperature can be displayed for viewing by a practitioner or operator on the user interface 122 of the control unit 120 (FIGS. 1–3). In a further aspect of this embodiment, the first foam portion 1240 can be configured to support the first and second temperature sensors 1260, 1262 toward the top surface of the first foam portion 1240. In one embodiment, the first and second temperature sensors 1260, 1262 can be resistive thermal devices (RTDs) provided by the Minco Corporation. In other embodiments, other temperature sensors can be used. For example, in another embodiment described in greater detail below, the heating pad 1210 can include one or more radiolucent temperature sensing devices.

In yet another aspect of this embodiment, the heating pad 1210 can further include a number of backup safety devices to prevent the heating pad 1210 from exceeding a selected temperature range. For example, in the illustrated embodiment, the heating pad 1210 can include a plurality of first thermostats 1204 connected in a series with the first power line 1231, and a plurality of second thermostats 1206 connected in a series with the second power line 1232. In one embodiment, the thermostats 1204, 1206 can include snap acting thermostats. In other embodiments, the thermostats 1204, 1206 can include other devices. The first plurality of thermostats 1204 can be configured to activate (i.e., open the corresponding circuit) if the heating element 1250 reaches a preselected over-temperature condition. For example, in one embodiment, the first plurality of thermostats 1204 can be configured to activate if the temperature of the heating element 1250 exceeds 49° C. If this temperature is exceeded, then one or more of the first plurality of thermostats 1204 can activate, thereby cutting power to the first lead 1253 and stopping the generation of heat.

In yet another aspect of this embodiment, the second plurality of thermostats 1206 can be configured to activate if the temperature proximate to the upper surface of the first foam portion 1240 exceeds a preselected temperature. For example, in one embodiment, the second plurality of thermostats 1206 can be configured to activate if the upper surface of the first foam portion 1240 exceeds 41° C. If this temperature is exceeded, then one or more of the second plurality of thermostats 1206 can activate, thereby cutting power to the second lead 1255 and stopping the generation of heat. The first foam portion 1240 can be dimpled or otherwise contoured to receive the plurality of second thermostats 1206 so that they will not be felt by a patient positioned on top of the heating pad 1210.

An operator (not shown) can use the heating pad 1210 to warm a patient (also not shown) in one embodiment as follows. First, the operator selects a desired heating pad temperature with, for example, the user interface 122 on the control unit 120 (FIGS. 1–3). The first and second temperature sensors 1260, 1262 then sense the temperature proximate to the surface of the heating pad 1210 and communicate this information to the control unit 120. If at any time during operation the surface temperature of the heating pad 1210 exceeds the selected temperature, the control unit 120 can shut off power to the heating element 1250 until the surface of the heating pad 1210 cools down to the selected temperature. Once the temperature falls to the selected temperature, the control unit 120 can continue applying power to the heating element 1250 to maintain the selected temperature. Thus, in this embodiment, the first and second temperature sensors 1260, 1262 are part of a primary temperature control circuit that modulates power to the heating element 1250 in response to the measured temperature proximate to the surface of the heating pad 1210.

In another embodiment, the plurality of second thermostats 1206 can make up a backup temperature control circuit for the heating pad 1210. For example, as mentioned above, the plurality of second thermostats 1206 can be configured to activate and open the corresponding electrical circuit to the second lead 1255 if the temperature at the surface of the heating pad 1210 exceeds a preselected temperature. For example, if the highest possible temperature that the operator of the heating pad 1210 can select is 39° C., then the second plurality of thermostats 1206 can be configured to activate if the surface of the heating pad 1210 reaches 41° C. In this way, the second plurality of thermostats 1206 will not activate unless the primary temperature control circuit (i.e., the first and second temperature sensors 1260, 1262) fails.

As yet another backup temperature control circuit, the plurality of first thermostats 1204 can be configured to activate if the temperature proximate to the surface of the heating element 1250 exceeds a preselected temperature that is higher than the activation temperature of the plurality of second thermostats 1206. For example, if the plurality of second thermostats 1206 are configured to activate at 41° C., the plurality of first thermostats 1204 can be configured to activate at 49° C. Thus, if the primary temperature control circuit provided by the first and second temperature sensors 1260, 1262 fails, and the backup circuit provided by the plurality of second thermostats 1206 also fails, then the plurality of first thermostats 1204 can activate to open the corresponding electrical circuit and cut power to the heating element 1250.

The temperature control circuits described above are provided here to illustrate one method for controlling the temperature of the heating pad 1210 in accordance with the present invention. However, the invention is not limited to the particular embodiment described. Accordingly, in other embodiments, other temperature sensors and/or other thermostats can be used to provide primary and backup temperature control circuits configured in accordance with the present invention.

In yet another aspect of this embodiment, the heating element 1250 can be at least partially enclosed within a first sleeve 1270. In one embodiment, the first sleeve 1270 can include carbon fiber material such as Kevlar®. In other embodiments, the first sleeve 1270 can include other materials. In a further aspect of this embodiment, the heating pad 1210 can also include a second sleeve 1272 configured to at least partially enclose the first and second foam portions 1240, 1242 and the heating element 1250. In one embodiment, the second sleeve 1272 can include carbon fiber material such as Kevlar®. In other embodiments, the second sleeve 1272 can include other materials. In yet another embodiment, the first sleeve 1270 and/or the second sleeve 1272 can be omitted.

In a further aspect of this embodiment, the cover 1212 can extend over the second sleeve 1272. In one embodiment, the cover 1212 can include an antimicrobial, abrasion-resistant and comfortable fabric, such as Kody fabric. The cover 1212 can further include a fluid-resistant zipper 1213 extending longitudinally on a lower surface of the cover 1212 to facilitate its removal.

Figure 13:
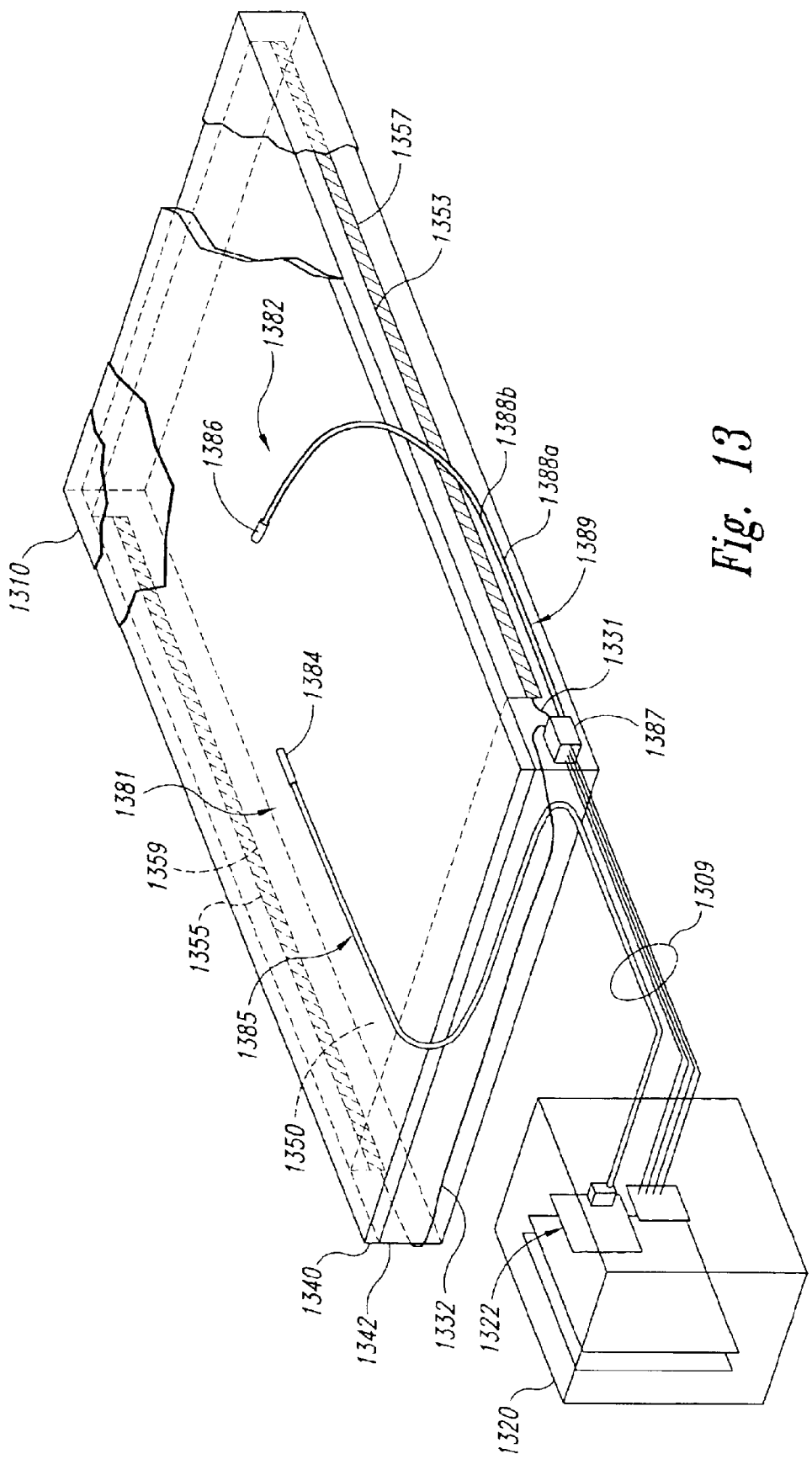
FIG. 13 is a partially cut away, top isometric view of a heating pad configured in accordance with another embodiment of the invention.

FIG. 13 is a partially cut away, top isometric view of a heating pad 1310 configured in accordance with another embodiment of the invention. Many elements of the heating pad 1310 can be at least generally similar in structure and function to the heating pad 1210 discussed above with reference to FIG. 12. For example, the heating pad 1310 can include a heating element 1350 sandwiched between a first foam portion 1340 and a second foam portion 1342. The first foam portion 1340 may be relatively thin in this embodiment and may have a thickness of from about 0.12 inch to about 1 inch. In another embodiment, the first foam portion 1340 can have a thickness of about 0.50 inch. In further embodiments, the first foam portion may have other thicknesses or it can be omitted.

The heating element 1350 can be at least generally similar in structure and function to the heating element 1250 described above with reference to FIG. 12. For example, the heating element 1350 can include a first bus bar or first lead 1353 extending proximate to a first edge 1357 of the heating element 1350, and a second bus bar or second lead 1355 extending proximate to a second edge 1359 of the heating element 1350. In a further aspect of this embodiment, however, the first and second edges 1357, 1359 of the heating element 1350 are folded downward along the sides of the second foam portion 1342. One advantage of this feature is that it orients the leads 1353, 1355 edgewise on the outer periphery of the heating pad 1310 so that the majority of the heating pad 1310 remains radiolucent to facilitate x-ray imaging of a patient positioned on the heating pad 1310.

In a further aspect of this embodiment, the heating pad 1310 can include a number of features that enhance its radiolucent characteristics to facilitate its use in warming patients undergoing x-ray examinations, such as x-ray exams occurring during a typical cardiac catheterization procedure. For example, in the illustrated embodiment, the heating pad 1310 can include a first or primary temperature control circuit 1381 and a second or backup temperature control circuit 1382 that are both at least generally radiolucent. The primary temperature control circuit 1381 can include a first radiolucent temperature sensing device 1384 ("first radiolucent device 1384") operably connected to a heating pad control unit 1320 by a first radiolucent cable 1385. The first radiolucent device 1384 can be positioned at least proximate to the upper surface of the first foam portion 1340. In one aspect of this embodiment, the first radiolucent device 1384 can include a fiber optic temperature sensor. In other embodiments, it is expected that the first radiolucent device 1384 can include other types of radiolucent, or at least generally radiolucent, temperature sensing devices. In another aspect of this embodiment, the first radiolucent cable 1385 can include a fiber optic cable for communicating temperature information from the first radiolucent device 1384 to the control unit 1320. In other embodiments, it is expected that the first radiolucent cable 1385 can include other radiolucent, or at least generally radiolucent, cables suitable for communicating temperature information from the first radiolucent device 1384 to the control unit 1320. In yet other embodiments, it is expected that the heating pad 1310 can include one or more wireless devices for communicating temperature information from the heating pad 1310 to the control unit 1320 or, alternatively, for communicating temperature control inputs from the control unit 1320 to the heating element 1350. When the first radiolucent device 1384 includes a fiber optic temperature sensing device, the control unit 1320 can include a fiber optic controller 1322 configured to convert the optical signal received from the fiber optic device into an electric signal usable by the control unit 1320. The first radiolucent device 1384 can be operably connected to the fiber optic controller 1322 via a pan-down or other suitable connector 1309 (shown schematically in FIG. 13).

When the heating element 1350 is operating, the first radiolucent device 1384 can sense the temperature proximate to the surface of the heating pad 1310 and communicate temperature information to the control unit 1320 via the first radiolucent cable 1385. The control unit 1320 can then display the heating pad temperature as described above with reference to, for example, FIG. 3, for viewing by an operator or practitioner (not shown). Further, the control unit 1320 can use the temperature information received from the first radiolucent device 1384 to control the temperature of the heating element 1350. For example, if the first radiolucent device 1384 determines that the temperature proximate to the surface of the heating pad 1310 exceeds the temperature selected by the operator, then the control unit 1320 can cut off power to the heating element 1350 until the temperature drops down to the selected temperature.

In another aspect of this embodiment, the backup temperature control circuit 1384 can include a second radiolucent temperature sensing device 1386 ("second radiolucent device 1386") operably connected to the control unit 1320 by a second radiolucent cable 1389. In one aspect of this embodiment, the second radiolucent device 1386 can include a thermally responsive media such as a thermal chromatic liquid crystal (TLC) that changes state at a predetermined temperature. In other embodiments, it is expected that the second radiolucent device 1386 can include other types of radiolucent, or at least generally radiolucent, temperature sensing and/or thermally responsive state-changing devices. For example, in one other embodiment, the second radiolucent device 1386 can include a fiber optic temperature sensor at least generally similar to the first radiolucent device 1384.

In a further aspect of this embodiment, the second radiolucent cable 1389 can include at least one fiber optic cable for communicating temperature information from the second radiolucent device 1386 to an electronic module 1387 embedded toward a lower corner of the heating pad 1310. For example, in the illustrated embodiment, the second radiolucent cable 1389 includes a first fiber optic tube 1388*a* and a second fiber optic tube 1388*b* extending between the second radiolucent device 1386 and the electronic module 1387. The electronic module 1387 can be operably connected to the control unit 1320 to receive electrical power from the control unit 1320. In addition, the electronic module 1387 can be operably connected to the first lead 1353 by a first power line 1331 and to the second lead 1355 by a second power line 1332.

In operation, the electronic module 1387 acts like a switch that controls power to the first and second leads 1353, 1355 in response to changing light signals received from the second radiolucent device 1386 via the second fiber optic tubes 1388*b*. For example, when the second radiolucent device 1386 includes a TLC, the electronic module 1387 can emit a light signal through the first fiber optic tube 1388*a* to the TLC. The light signal can pass through the TLC and return to the electronic module 1387 via the second fiber optic tube 1388*b*. If the TLC changes state in response to reaching a predetermined temperature, the light signal returning to the electronic module 1387 via the second fiber optic tube 1388*b* will change accordingly. The electronic module can then cut power to the leads 1353, 1355 on the heating element 1350 in response to receiving the changed light signal.

In operation, the primary temperature control circuit 1381 can be used to limit the temperature of the heating pad 1310 to a first operating range, and the backup temperature control circuit 1382 can be used to limit the temperature of the heating pad 1310 to a second higher temperature range in the event that the primary temperature control circuit 1381 fails. For example, in this embodiment, an operator selects a heating pad temperature with the control unit 1320 and power is transmitted to the heating element 1350 via the first and second power lines 1331, 1332. As the heating pad 1310 warms up, the first radiolucent device 1384 senses the temperature proximate to the surface of the heating pad 1310 and communicates this information to the control unit 1320 via the first radiolucent cable 1385. If the sensed temperature exceeds the selected temperature, then the control unit 1320 cuts off power to the heating element 1350 until the temperature proximate to the surface of the heating pad 1310 drops to, or below, the selected temperature. At such time, the control unit 1320 resumes transmitting power to the heating element 1350. In this manner, the temperature proximate to the surface of the heating pad 1310 is maintained at or near the selected temperature.

If the primary temperature control circuit 1381 fails, then the heating pad 1310 may continue to warm above and beyond the selected temperature. If this happens and the temperature proximate to the surface of the heating pad 1310 reaches or exceeds the threshold temperature at which the second radiolucent device 1386 is activated (e.g., changes state), then the second radiolucent device 1386 will interrupt or otherwise change the light signal received from the electronic module 1387 via the first fiber optic tube 1388*a*. The changed light signal will then return to the electronic module 1387 via the second fiber optic tube 1388*b*. The change in the light signal returning to the electronic module 1387 will cause the electronic module 1387 to cut off power to the heating element 1350 until the temperature proximate to the surface of the heating pad 1310 drops to, or below, the selected temperature.

In a further aspect of this embodiment, the primary temperature control circuit 1381 can be configured to control the temperature proximate to the surface of the heating pad 1310 to within a first range of, for example, +2° F. above the selected temperature, and the backup temperature control circuit 1382 can be configured to control the temperature proximate to the heating element 1350 to within a second higher range of, for example, +10° C. above the selected temperature. Thus, in this embodiment, if the primary temperature control circuit 1381 fails, then the backup temperature control circuit 1382 will prevent the heating pad 1310 from exceeding the selected temperature by more than 10° C. These temperature control limits provided here are for purposes of illustration only. Accordingly, in other embodiments, the primary and backup temperature control circuits 1381, 1382 can have other temperature control limits. In one other embodiment, the primary and backup temperature control circuits 1381, 1382 can have the same temperature control limit.

One feature of the embodiments of the invention illustrated in FIG. 13 is that the heating element 1350, the primary temperature control circuit 1381, and the secondary temperature control circuit 1382 are all at least generally radiolucent. One advantage of this feature is that the heating pad 1310 can be used to warm and support a patient undergoing a full-body x-ray exam, such as an x-ray exam associated with a cardiac catheterization procedure, and the heating pad 1310 will not obscure or otherwise appreciably impair the x-ray imaging.

Figure 14:
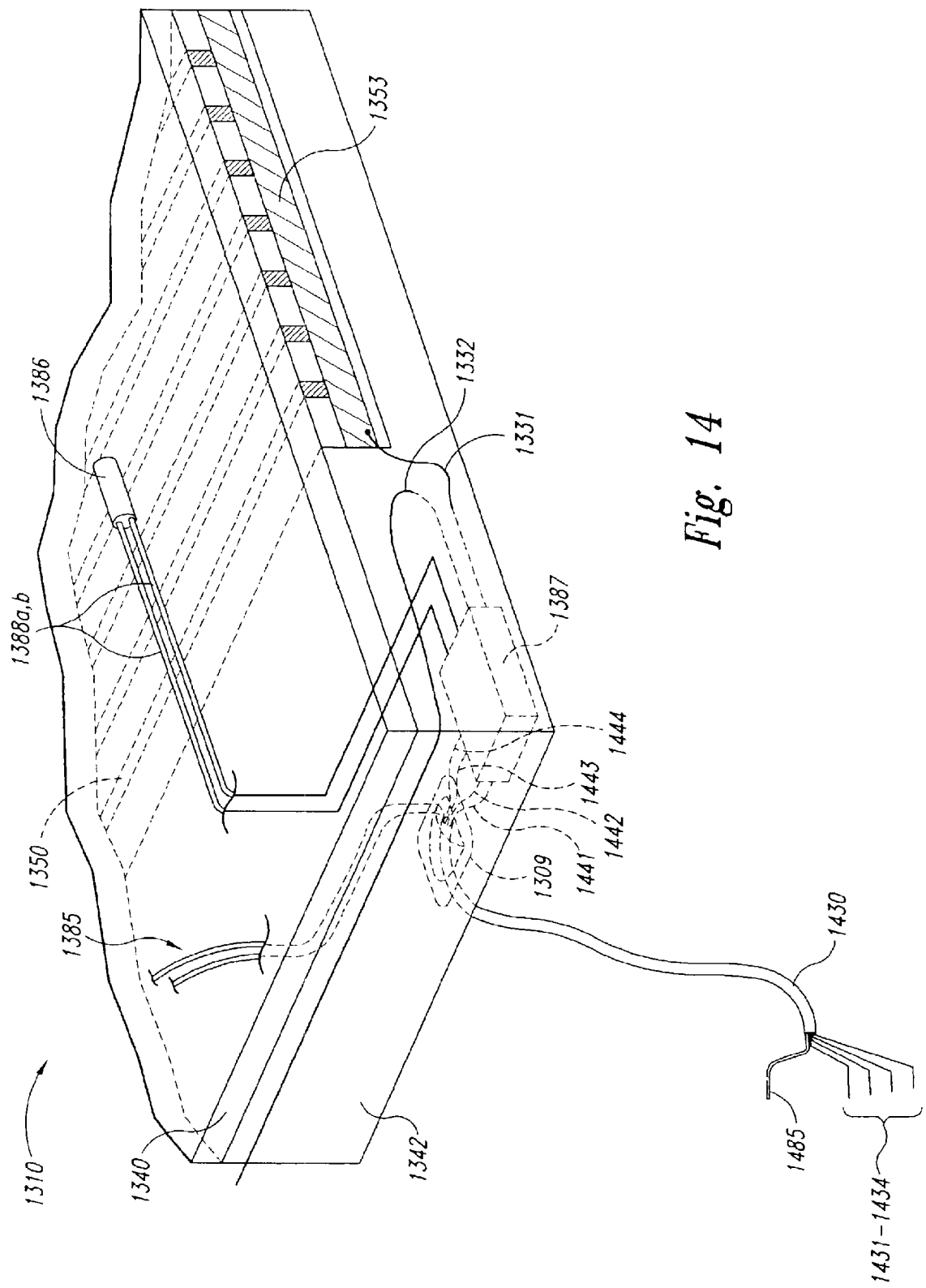
FIG. 14 is a partially schematic enlarged top isometric view of a corner portion of the heating pad of FIG. 13 configured in accordance with an embodiment of the invention.

FIG. 14 is a partially schematic, enlarged, top isometric view of a corner portion of the heating pad 1310 of FIG. 13 configured in accordance with an embodiment of the invention. In one aspect of this embodiment, the electronic module 1387 can be embedded in a lower corner of the second foam portion 1342. In other embodiments, the electronic module 1387 can be located in other positions. For example, in one other embodiment, the electronic module 1387 can be located outside of the heating pad 1310. The fiber optic tubes 1388*a, b* can extend from the electronic module 1387 to the second radiolucent device 1386. The second radiolucent device 1386 can be positioned at least proximate to the heating element 1350. For example, in the illustrated embodiment, the second radiolucent device 1386 is positioned at least generally on top of the heating element 1350. In other embodiments, the second radiolucent device 1386 can be positioned at other locations within the heating pad 1310.

In another aspect of this embodiment, a pan-down 1409 can be embedded in the second foam portion 1342 adjacent to the electronic module 1387. A utility cord 1430 extending from the control unit 1320 (not shown in FIG. 14) to the pan-down 1409 can include a cable 1485 and four power lines 1431–1434. The utility cord 1430 can be coupled to a connector on the pan-down 1409 so that the cable 1485 is operably connected to the first radiolucent cable 1385 extending from the pan-down 1409 to the first radiolucent device 1384 (not shown in FIG. 14). The utility cord 1430 can be similarly coupled to the connector on the pan-down 1409 so that the power lines 1431–1434 are operably connected to corresponding power lines 1441–1444 extending from the pan-down 1409 to the electronic module 1387. The power lines 1441 and 1442 can provide power to the electronic module 1387 from the control unit 1320. The power lines 1443 and 1444 can provide power to the leads 1353, 1355 via the electric module 1387. In other embodiments, other methods and structures can be used to operably connect the control unit 1320 to the various devices positioned within the heating pad 1310.

Figure 15:
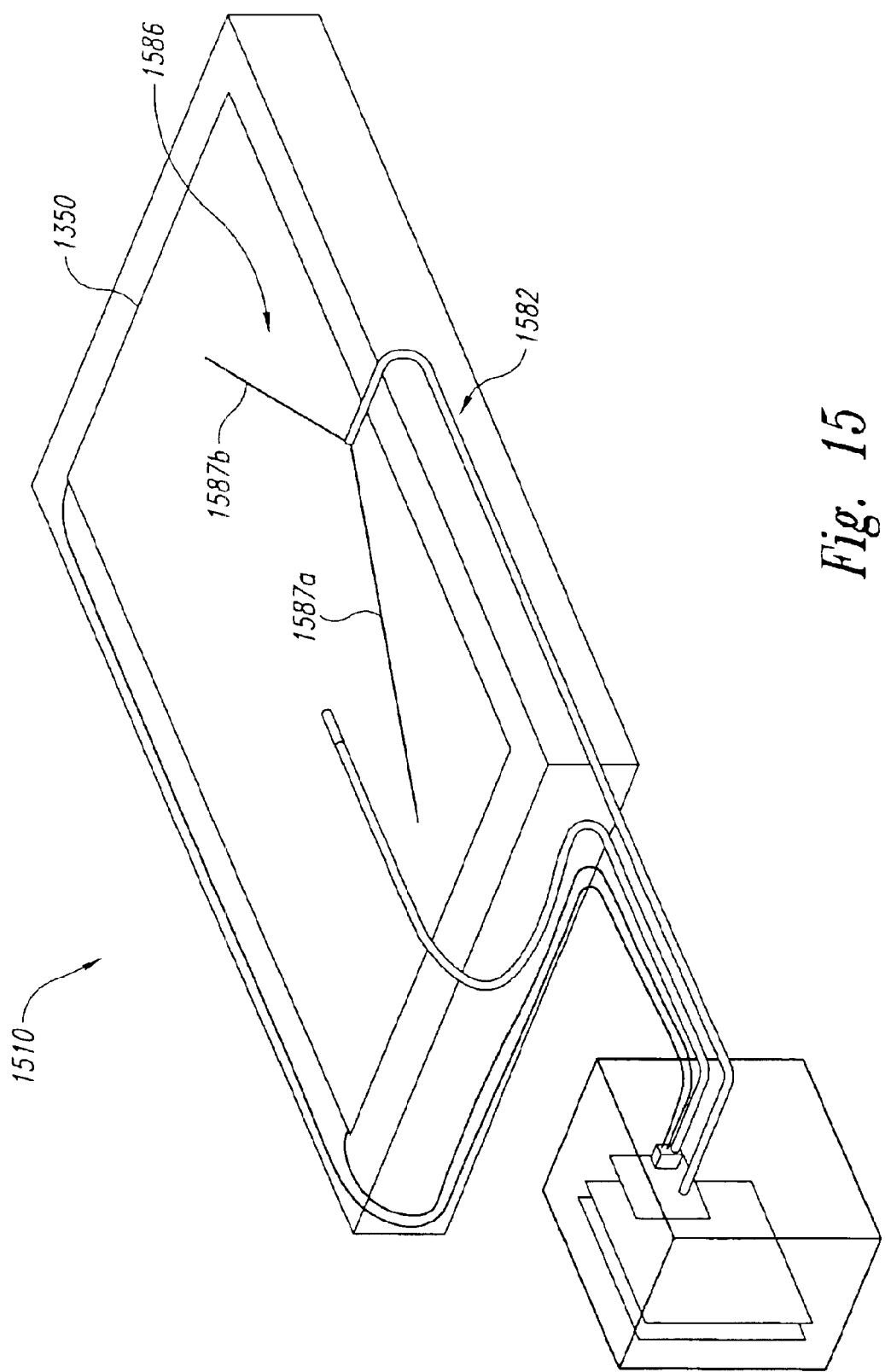
FIG. 15 is a partially schematic, top isometric view of a heating pad configured in accordance with yet another embodiment of the invention.

FIG. 15 is a partially schematic, top isometric view of a heating pad 1510 configured in accordance with yet another embodiment of the invention. An upper foam portion of the heating pad 1510 is omitted in FIG. 15 for purposes of clarity. Portions of the heating pad 1510 can be at least generally similar in structure and function to corresponding portions of the heating pad 1310 described above with reference to FIGS. 13 and 14. In one aspect of this embodiment, however, a second radiolucent device 1586 used in a backup temperature control circuit 1582 can include a plurality of fiber optic pipe strands 1587 (shown as a first fiber optic pipe strand 1587*a* and a second fiber optic pipe strand 1587*b*). It is expected that use of multiple fiber optic pipe strands will allow temperature averaging across a heating element 1350.

Figure 16:
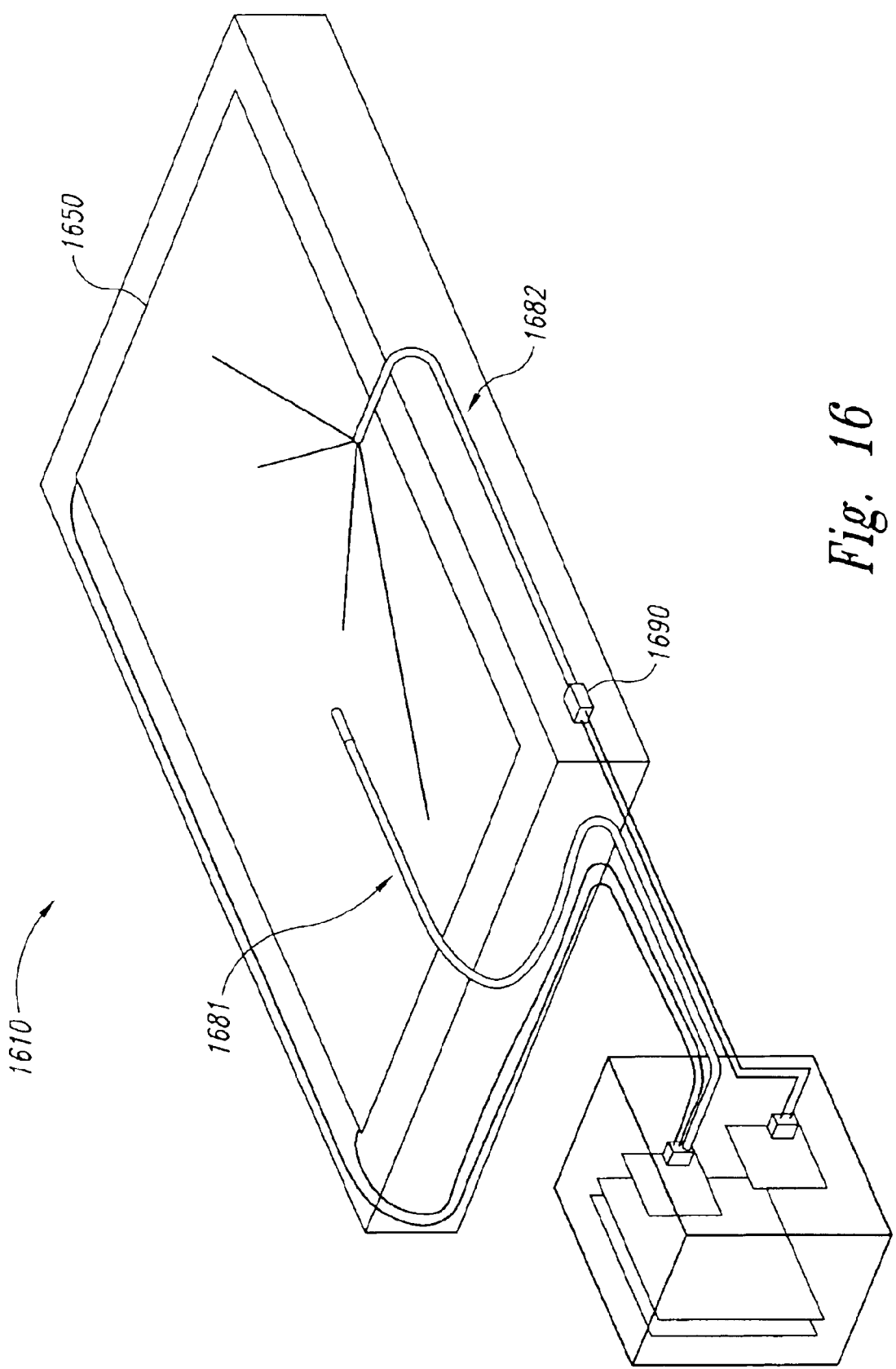
FIG. 16 is a partially schematic, top isometric view of a heating pad configured in accordance with yet another embodiment of the invention.

FIG. 16 is a partially schematic, top isometric view of a heating pad 1610 configured in accordance with yet another embodiment of the invention. An upper foam portion of the heating pad 1610 is omitted in FIG. 16 for purposes of clarity. In one aspect of this embodiment, the heating pad 1610 includes an infrared sensor 1690 as an additional backup temperature control device. In this embodiment, the infrared sensor 1690 can be used to monitor and control the temperature of a heating element 1650 in the event that both a primary temperature control circuit 1681 and a backup temperature control circuit 1682 fail. (The primary and backup temperature control circuits 1681, 1682 can be at least generally similar in structure and function to the primary and backup temperature control circuits 1381, 1382, respectively, described above with reference to FIG. 13.) As will be apparent to those of ordinary skill in the relevant art, radiolucent temperature control devices in accordance with the present invention are not limited to the fiber optic or infrared temperature sensors disclosed herein. Accordingly, in other embodiments, other radiolucent, or at least generally radiolucent, temperature control devices can be used to control the temperature of heating pads configured in accordance with the present disclosure.

FIGS. 17A–D illustrate a patient positioning/warming device configured in accordance with an embodiment of the invention. The positioning/warming device of the illustrated embodiment may be a leg positioning device configured to facilitate the harvest of veins from a patient's leg for use in heart surgery or another medical procedure. This particular positioning/warming device configuration is presented here only to illustrate selected aspects of the invention. Accordingly, as will be explained in greater detail below, in other embodiments patient positioning/warming devices in accordance with the invention can have other configurations.

Figure 17A:
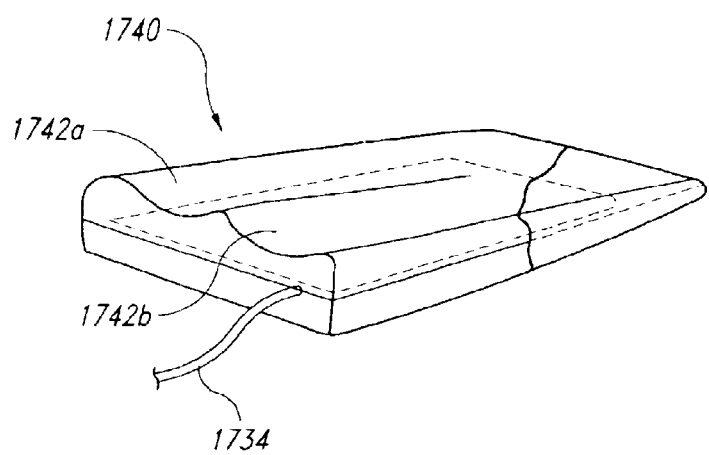
FIG. 17A is a top isometric view of a positioning/warming device configured in accordance with an embodiment of the invention.
Figure 17B:
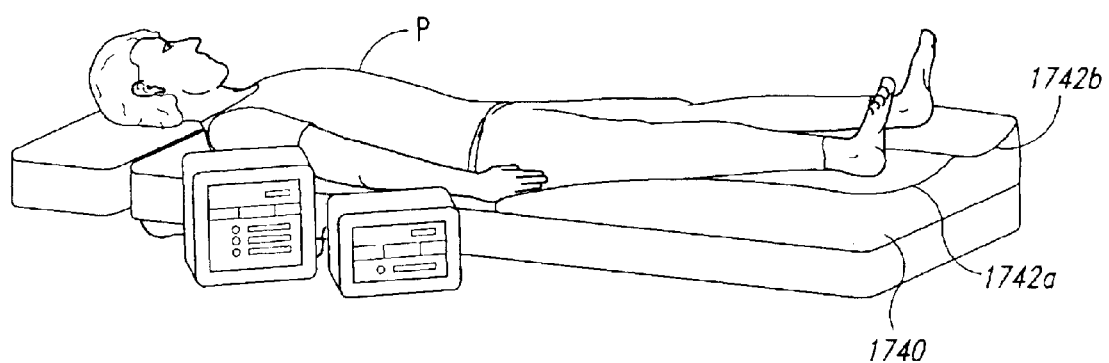
FIG. 17B is a top isometric view of the positioning/warming device of FIG. 17A supporting the legs of a patient in accordance with an embodiment of the invention.

FIG. 17A is a top isometric view of a positioning/warming device 1740 configured in accordance with an embodiment of the invention. In one aspect of this embodiment, the positioning/warming device 1740 receives electrical power via a power line 1734 (from, e.g., a control unit such as the accessory control unit 1022*a* of FIG. 10). In the illustrated embodiment, the positioning/warming device 1740 includes a first contoured portion 1742*a* and a second contoured portion 1742*b*. As shown in FIG. 17B, the first and second contoured portions 1742*a, b* are configured to receive the legs of a patient P and provide warmth to the legs while positioning them in a favorable orientation for harvesting veins or for conducting other medical procedures.

Figure 17C:
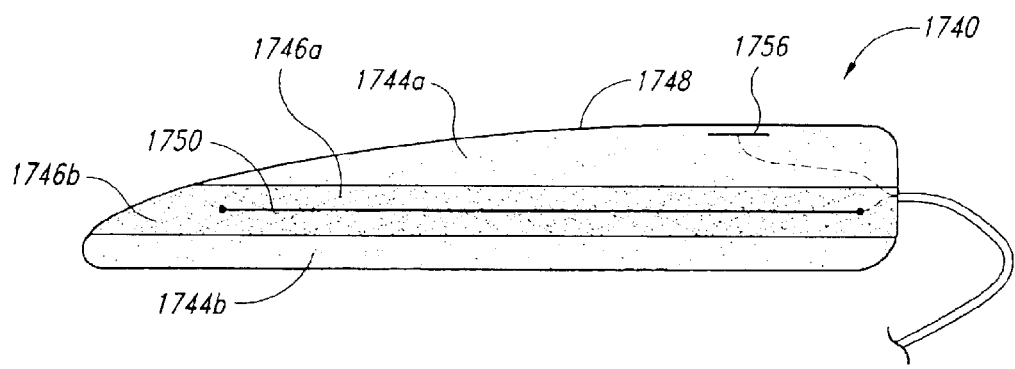
FIG. 17C is a side cross-sectional view of the positioning/warming device of FIG. 17A configured in accordance with an embodiment of the invention.
Figure 17D:
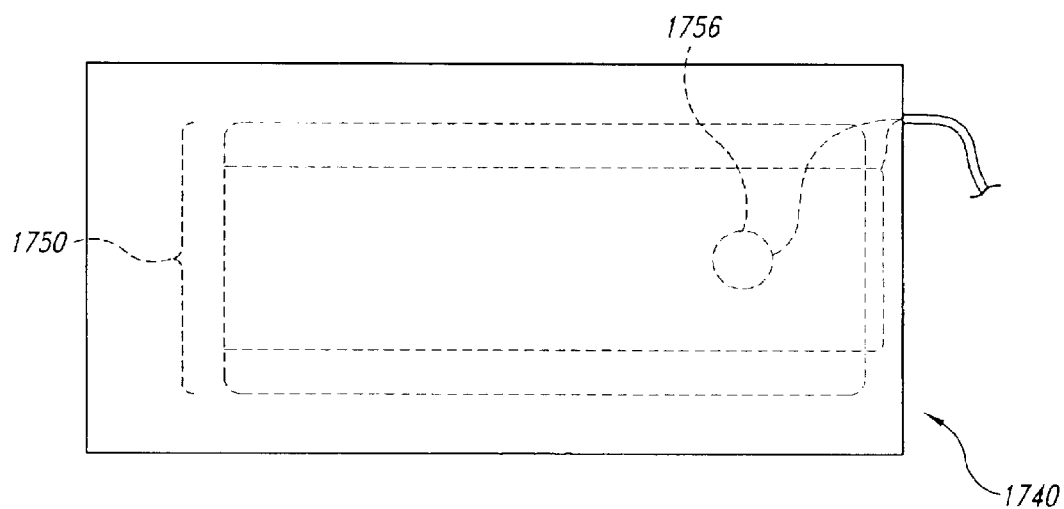
FIG. 17D is a partially hidden top plan view of the positioning/warming device of FIG. 17A configured in accordance with an embodiment of the invention.

FIG. 17C is a side cross-sectional view, and FIG. 17D is a partially hidden top plan view, of the positioning/warming device 1740 configured in accordance with an embodiment of the invention. Referring to FIGS. 17C and D together, in one aspect of this embodiment, the positioning/warming device 1740 includes a heating element 1750, inner foam portions 1746*a, b,* and outer foam portions 1744*a, b*. The heating element 1750 can be at least generally similar in structure and function to one or more of the heating elements described in detail above. The foam portions 1746, 1744 can be selected depending on a number of factors including, for example, pressure reduction and heat retention parameters. In one embodiment, for example, the inner foam portions 1746 may be denser than the outer foam portions 1744 to retain the heat from the heating element 1750. In this embodiment, at least one of the inner foam portions 1746 can be a viscoelastic foam selected and positioned to act as a heat reservoir efficiently retaining heat generated by the heating element 1750. In another aspect of this embodiment, the outer foam portions 1744 can be selected from a number of different types of viscoelastic foam designed for pressure reduction and patient comfort. In other embodiments, the inner and outer foam portions 1746, 1744 can include foams having the same densities. In yet other embodiments, one or more of the inner foam portions 1746, or alternatively, one or more of the outer foam portions 1744, can be omitted from the positioning/warming device 1740.

The foam selected for use in the positioning/warming device 1740 can be contoured to provide a desired shape for patient positioning using a number of different methods. In one embodiment, the foam can be formed by injection molding with an appropriate mold. In another embodiment, the foam can be machined or otherwise cut to provide the desired shape.

In a further aspect of this embodiment, the positioning/warming device 1740 can include a fluid-resistant and antimicrobial cover 1748. In one embodiment, the cover 1748 can be a spray-on coating that can be easily cleaned. In another embodiment, the cover 1748 can include a durable fabric material shaped and sized to fit neatly around the contoured foam portions 1744, 1746.

In one embodiment, the patient positioning/warming device 1740 can include one or more temperature sensors 1756 for providing temperature feedback to the corresponding control unit. The temperature sensors 1756 and associated systems can be at least generally similar in structure and function to the temperature sensors and associated feedback circuits described in U.S. patent application Ser. No. 09/880,725 and U.S. provisional patent application No. 60/374,853. The temperature sensor circuit can provide a means for preventing the temperature proximate to the surface of the pad from exceeding a selected temperature. If the temperature exceeds the selected temperature, the circuit can automatically reduce power to the heating element 1750 until the temperature returns to the selected level.

As discussed above, it is often desirable to warm patients while they are undergoing x-ray exams. If the patients are situated on heating pads that include temperature sensors and associated circuitry that are not radiolucent, however, this hardware may inhibit or otherwise prevent obtaining usable x-ray images. To overcome this problem, patient positioning/warming devices in accordance with the present invention can include a number of features to enhance radiolucency. As described above, such devices can include fiber optic cables, fiber optic temperature sensing devices, thermal chromatic state-changing switch devices, nonmetallic heating elements, and/or other similar devices.

Various aspects of the positioning/warming device 1740 described above can be at least generally similar in structure and function to one or more of the heating pads and/or heating mattresses described in detail in pending patent application Ser. No. 09/880,725 or in pending provisional application No. 60/374,853. In addition, the various embodiments of the invention described herein can be modified and combined with aspects of the embodiments disclosed in these pending applications to provide different embodiments than those disclosed herein. Further, FIGS. 17A–D describe only one embodiment of a patient positioning/warming device in accordance with the present invention. In other embodiments, such devices can include other features without departing from the present disclosure. For example, in very general terms, patient positioning/warming devices in accordance with the present invention can include a shaped pressure relief portion (e.g., a foam portion) configured to support part of a patient during a medical procedure and a heating element portion configured to provide warmth to the patient during the medical procedure. Accordingly, the present invention is not limited to the particular embodiments described herein.

For example, in another embodiment, a device configured in accordance with the present invention can include a plurality of loose foam pieces (e.g., foam pieces such as those typically found in "bean bag chairs") contained within a cover. One advantage of using loose foam pieces rather than a shaped piece of foam may be that the device is more easily conformable to a particular position or a particular shape of the patient. In yet other embodiments, it is expected that some positioning/warming devices in accordance with the present invention may not include any foam but instead may utilize a rigid or quasi-rigid material that suitably conducts heat to the patient while comfortably positioning the patient. It is further expected that yet other embodiments may utilize fibrous materials in place of foam. Such fibrous materials may include both natural and manufactured fibers or fill material. For example, in one embodiment, such fibrous materials may include nylon fibers and/or wool fibers. In still further embodiments, it is expected that at least portions of heating pads and patient positioning/warming devices configured in accordance with the present invention can include air-filled compartments. Such compartments can be used as pressure relief or shaping features of the heating devices.

Figure 18A:
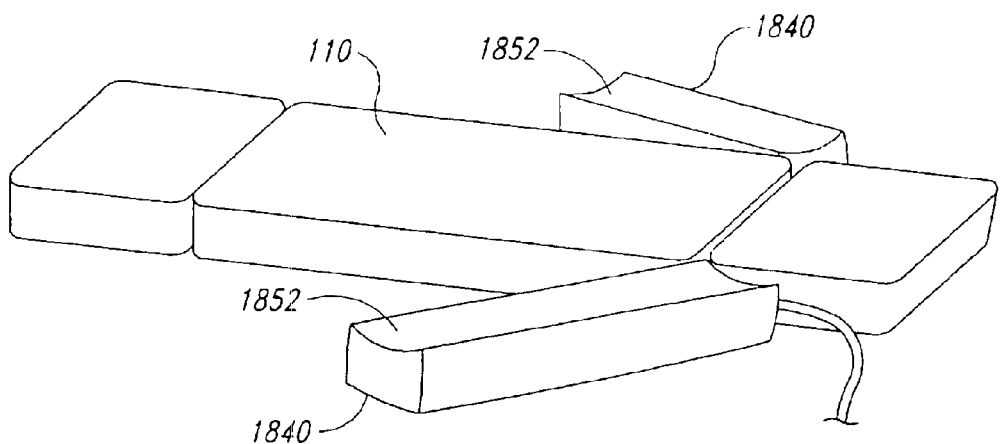
FIG. 18A is an isometric view of a patient warming system that includes two armboards configured in accordance with an embodiment of the invention.
Figure 18B:
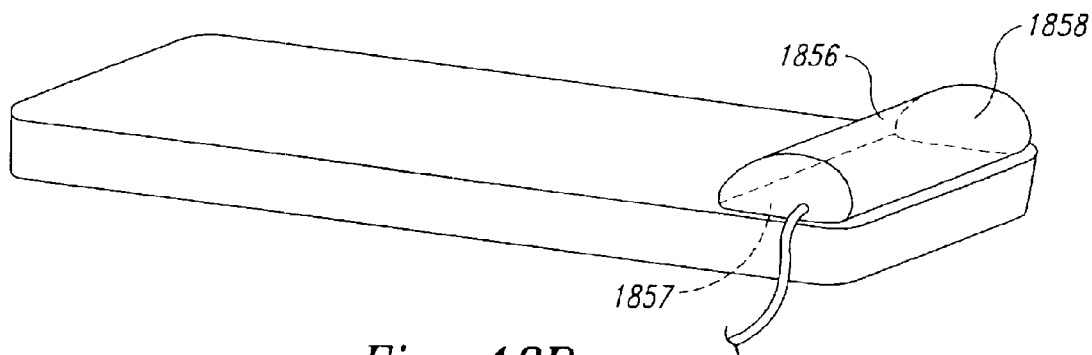
FIG. 18B is an isometric view of a patient warming system that includes a roll configured in accordance with another embodiment of the invention.
Figure 18C:
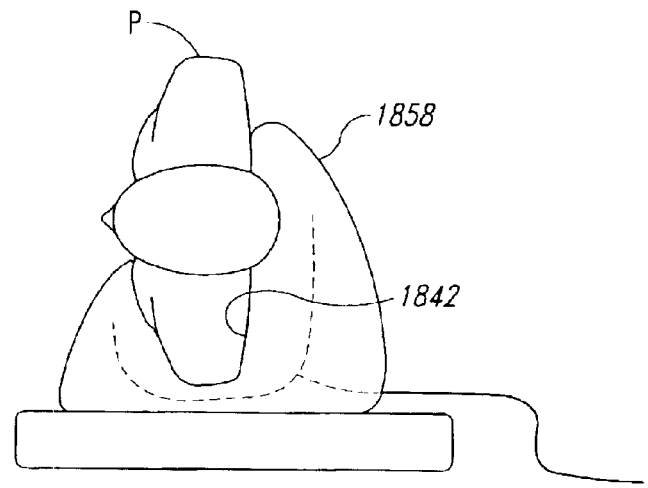
FIG. 18C is an end elevation view of a patient positioning/warming device configured in accordance with yet another embodiment of the invention.

As mentioned above, a wide variety of shapes and sizes of patient positioning/warming devices are possible in accordance with the present invention. A few of such devices are illustrated in FIGS. 18A–C. FIG. 18A, for example, is an isometric view of a patient warming system that includes two armboards 1840 configured in accordance with an embodiment of the invention. Each of the armboards 1840 includes a concave contoured portion 1852 configured to receive and accommodate a patient's arm. In one aspect of this embodiment, the basic construction of the armboards 1840 can be at least generally similar to the construction of the positioning/warming device 1740 described above with reference to FIGS. 17A–D. As shown in FIG. 18A, the armboards 1840 can be positioned proximate to the heating pad 110 in such a way as to provide warmth to a patient's arms when they are extended at least partially outwardly from the patient's body. In one embodiment, each of the armboards 1840 can receive an independent power line from an associated control unit. In another embodiment, a junction can be used to split a single power line between both of the armboards 1840.

FIG. 18B is an isometric view of a patient warming system that includes a roll 1856 configured in accordance with another embodiment of the invention. The roll 1856 of the illustrated embodiment has a flat portion 1857 for stability and a generally cylindrical portion 1858. The roll 1856 can be used to elevate and warm the patient's knees, head, feet or other appendages as desired to facilitate a particular medical procedure or to induce a particular therapeutic effect.

FIG. 18C is an end elevation view of a patient positioning/warming device 1858 configured in accordance with yet another embodiment of the invention. In one aspect of this embodiment, the positioning/warming device 1858 includes a contoured recessed portion 1842 configured to provide warmth to a patient P while positioning the patient P on his/her side. As will be apparent to those of ordinary skill in the relevant art based on the embodiments of the invention described above, many other configurations of patient positioning/warming devices are possible in accordance with the present invention in addition to those described above.

Figure 19:
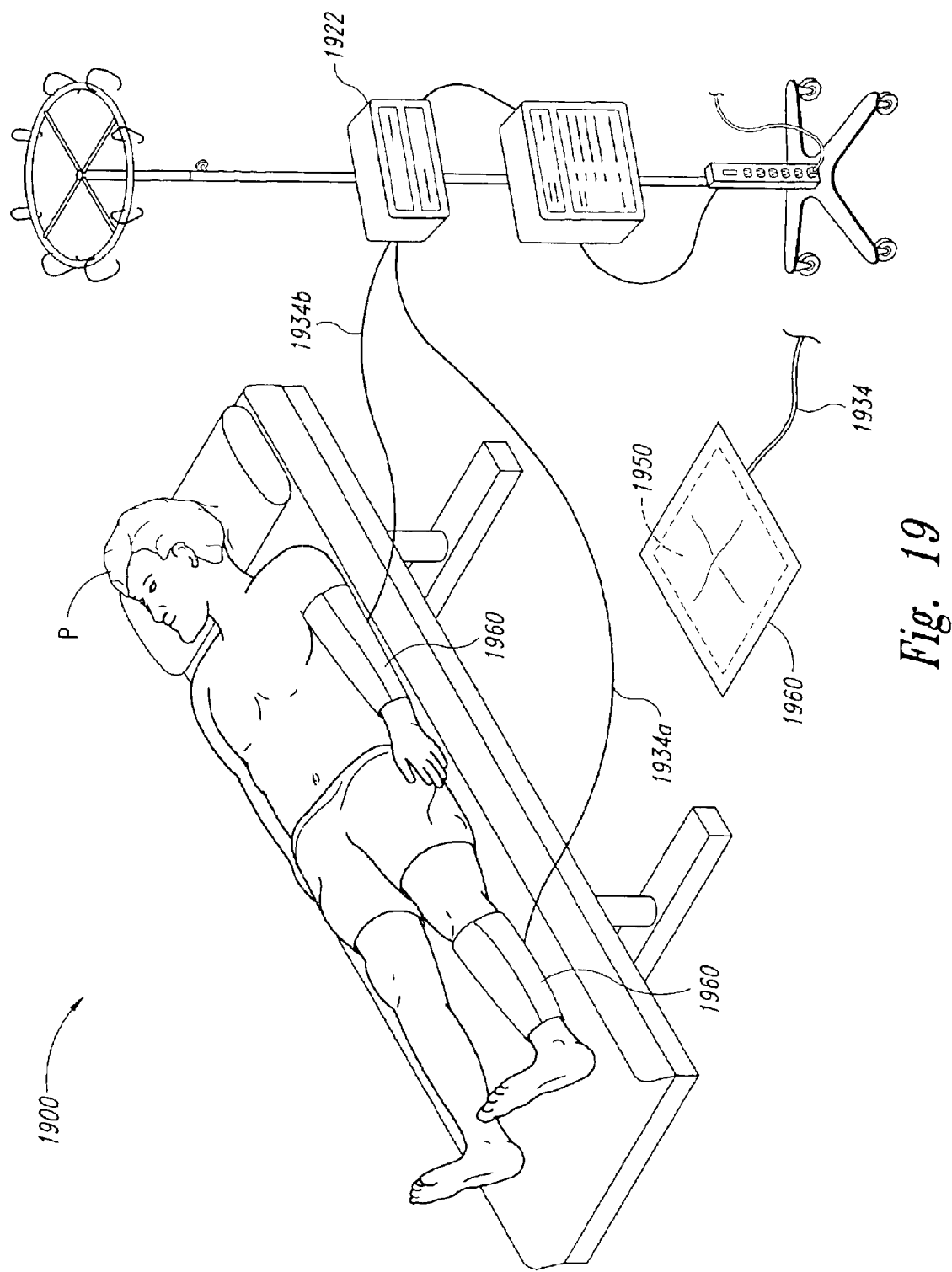
FIG. 19 is a partially schematic, isometric view of a patient warming system including one or more patient warming blankets configured in accordance with another embodiment of the invention.

FIG. 19 is a partially schematic, isometric view of a patient warming system 1900 including one or more patient warming blankets 1960 configured in accordance with another embodiment of the invention. In one aspect of this embodiment, the patient warming blankets 1960 can each include a heating element 1950 attached to an accessory control unit 1922 via power lines 1934*a, b*. The heating element 1950 may be at least partially enclosed in foam to provide the patient warming blankets 1960 with desirable heat retention and/or compression characteristics. Accordingly, in the illustrated embodiment, the patient warming blankets 1960 may be at least generally similar in construction to one or more of the heating devices described above with reference to FIGS. 1–18. One difference, however, may be that the patient warming blankets 1960 include much less foam such that they behave like typical blankets would when laid over a patient P or over a portion of the patient's body. For example, in another aspect of this embodiment, the patient warming blankets 1960 can be wrapped around an appendage of the patient P, such as the patient's arm or leg, to provide sufficient warming to the appendage during a particular medical procedure. In other embodiments, the patient warming blankets 1960 can simply be draped over a portion of the patient's body to provide desired warmth. In still further embodiments, the heating blankets 1960 can include one or more attachment features to hold the heating blankets snugly in place on the patient for improved heat retention. Such attachment features can include buckles, snaps, ties, adhesive tape, Velcro®, or other similar devices.

Figure 20:
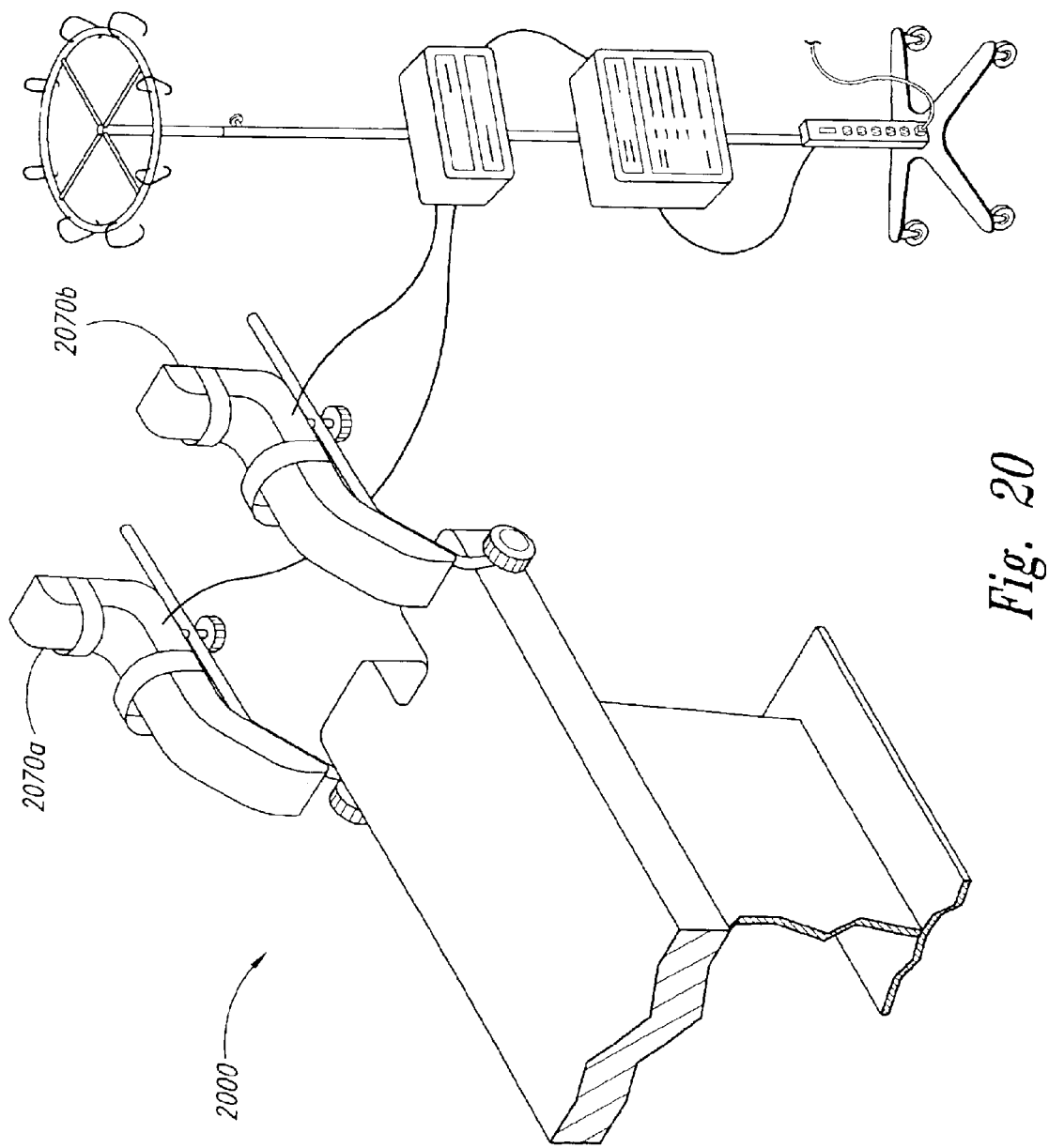
FIG. 20 is a partially schematic, isometric view of a patient warming system configured in accordance with yet another embodiment of the invention.

FIG. 20 is a partially schematic, isometric view of a patient warming system 2000 configured in accordance with yet another embodiment of the invention. In one aspect of this embodiment, the patient warming system 2000 can be used by a medical practitioner to position and warm a female patient (not shown) undergoing various gynecological procedures. In the illustrated embodiment, for example, the patient warming system 2000 includes stirrup warming devices 2070*a* and 2070*b*. The stirrup devices 2070 may be employed in a typical stirrup configuration known to those of skill in the art. In a further aspect of this embodiment, however, the stirrups 2070 can include contoured positioning/warming devices similar to those described above to provide warmth to the patient's legs and feet during the procedure. Such warmth may provide patient comfort and possibly reduce the likelihood of undesirable temperature-related side effects of the procedure.

Figure 21:
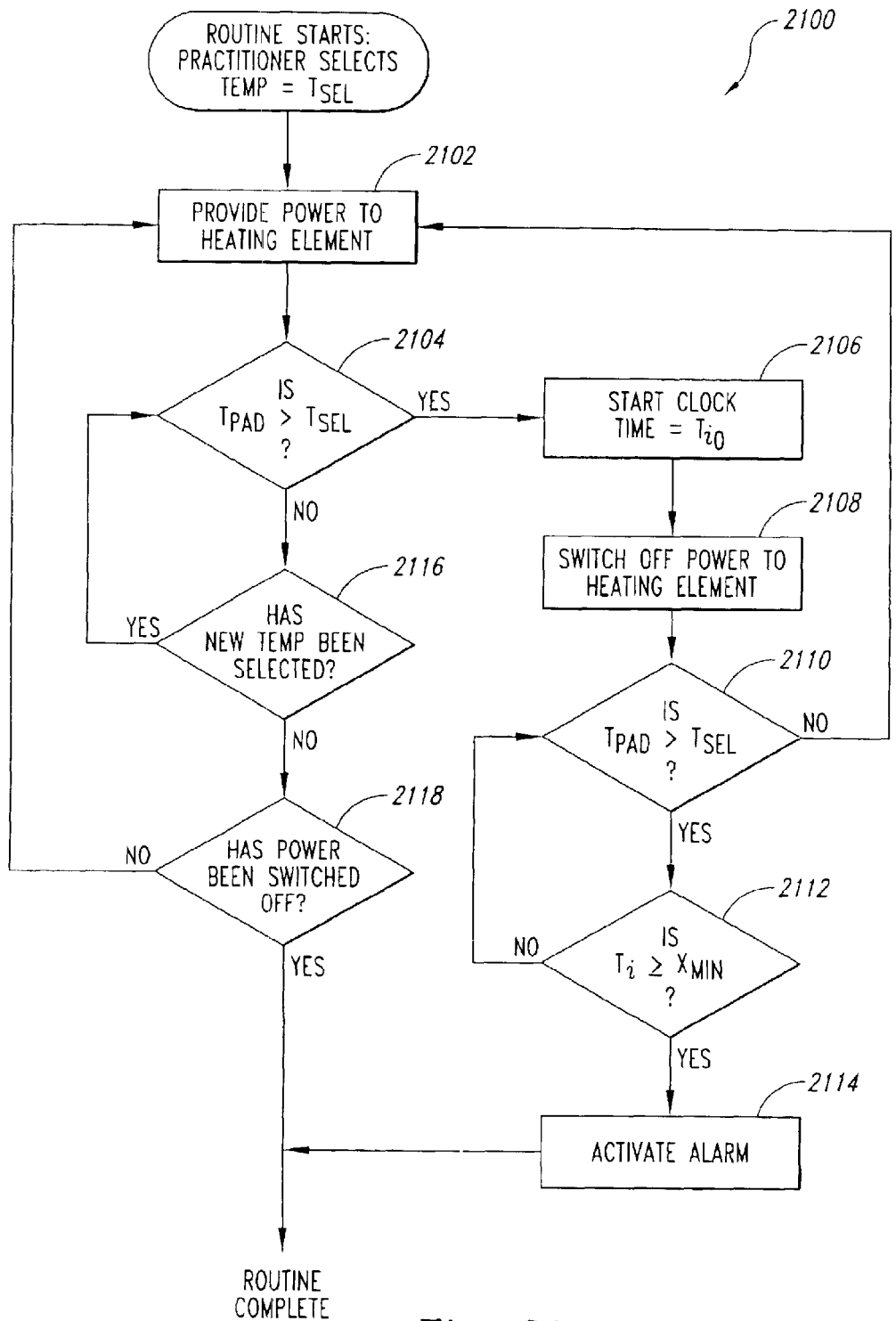
FIG. 21 illustrates a flow diagram of a routine for controlling the temperature of a heating pad in accordance with an embodiment of the invention.

FIG. 21 illustrates a flow diagram of a routine 2100 for controlling the temperature of a heating pad in accordance with an embodiment of the invention. The routine 2100 starts when an operator or practitioner selects a temperature for the heating pad with a corresponding control unit. In one embodiment, the operator can select this temperature by depressing the appropriate button on the control unit (e.g., the control unit 120 of FIG. 1). For ease of reference, the selected temperature will be referred to here as $T_{sel}$. In block 2102, the control unit provides power to the heating element in response to the operator's selection of a temperature. In decision block 2104, the routine determines if the temperature of the heating pad is greater than the selected temperature $T_{sel}$. (Or, alternatively, the routine can set a margin above the selected temperature, for example, 3° F., and determine if the temperature of the heating pad is greater than the selected temperature plus the margin.) If the temperature of the heating pad is greater than the selected temperature $T_{sel}$, then in block 2106 the routine starts a clock at time=$Ti_0$, and in block 2108, the control unit cuts off power to the heating element. In decision block 2110, the routine again checks the pad temperature to determine if it still exceeds the selected temperature. If the pad temperature no longer exceeds the selected temperature, then the routine returns to block 2102 and the control unit again provides power to the heating element to maintain the pad temperature at or near the selected temperature.

Referring to decision block 2110, if the pad temperature continues to exceed the selected temperature, then the routine proceeds to decision block 2112 to determine if the elapsed time Ti is greater than or equal to a preset time interval $X_{min}$. In one embodiment, the preset time interval $X_{min}$ can be about 10 minutes. In other embodiments, other time intervals can be chosen depending on various factors that may differ depending on the particular application. For example, in one other embodiment, the preset time interval $X_{min}$ can be about 5 minutes. If in decision block 2112 the elapsed time Ti is not equal to or greater than the preset time interval $X_{min}$, then the routine returns to decision block 2110 to again check the temperature of the heating pad. If the heating pad temperature still exceeds the selected temperature $T_{sel}$, then the routine again returns to decision block 2112 to determine if the elapsed time Ti is equal to or greater than the preset time interval $X_{min}$. If the elapsed time Ti is now equal to or greater than the preset time interval $X_{min}$, then in block 2114, the routine activates an alarm. As described above, this alarm can include a visible alarm, such as a flashing light, or an audible alarm. The alarm can notify the operator that the heating pad has exceeded the selected temperature for the preset time interval $X_{min}$. In this situation, the operator may elect to remove the patient from the heating pad and/or investigate to see if the reason for the high temperature is readily apparent.

Returning to decision block 2104, if the heating pad temperature does not exceed the selected temperature $T_{sel}$, then the routine proceeds to decision block 2116 to determine if the operator has selected a new heating pad temperature. If the operator has selected a new temperature, then the routine returns to decision block 2104 to determine if the heating pad temperature exceeds the newly selected temperature $T_{sel}$. If the heating pad temperature does exceed the newly selected temperature, then the routine proceeds as described above to reduce the heating pad temperature by cutting power to the heating element.

Returning to decision block 2116, if the operator has not selected a new heating pad temperature, then the routine proceeds to decision block 2118 to determine if the operator has switched the heating pad off. If the operator has switched the heating pad off, then power to the heating element is cut and the routine is complete. If the operator has not switched the heating pad off, then the routine returns to block 2102 and the control unit continues to provide power to the heating element. From here, the routine proceeds as described above to ensure that either 1) the heating pad temperature does not exceed the selected temperature $T_{sel}$ for the preset time interval $X_{min}$, or 2) if the heating pad temperature does exceed the selected temperature $T_{sel}$ for the preset time interval $X_{min}$, the alarm will activate.

One advantage of the embodiment of the invention described above with reference to FIG. 21 is that the alarm will not activate until the heating pad temperature has exceeded the selected temperature for a predetermined period of time. Thus, the alarm will not activate inadvertently due to a momentary spike in temperature. For example, in certain medical procedures, the use of a cauterizing device (e.g., a cauterizing pencil or a device known in the medical field as a "roller ball") can cause some temperature sensors in the proximity of the cauterizing device to register a momentary temperature spike. This momentary temperature spike does not reflect the actual temperature of the heating pad on which the patient may be lying. As will be appreciated by those who conduct such procedures, it would be undesirable to have the alarm activated every time one or more of the temperature sensing devices responded to an erroneous signal from the cauterizing device. The delayed alarm activation routine as described herein controls the alarm so that it will only be activated when the heating pad exceeds the selected temperature for a preset period of time. As a result, such momentary temperature spikes will not result an erroneous alarm activation.

Figure 22:
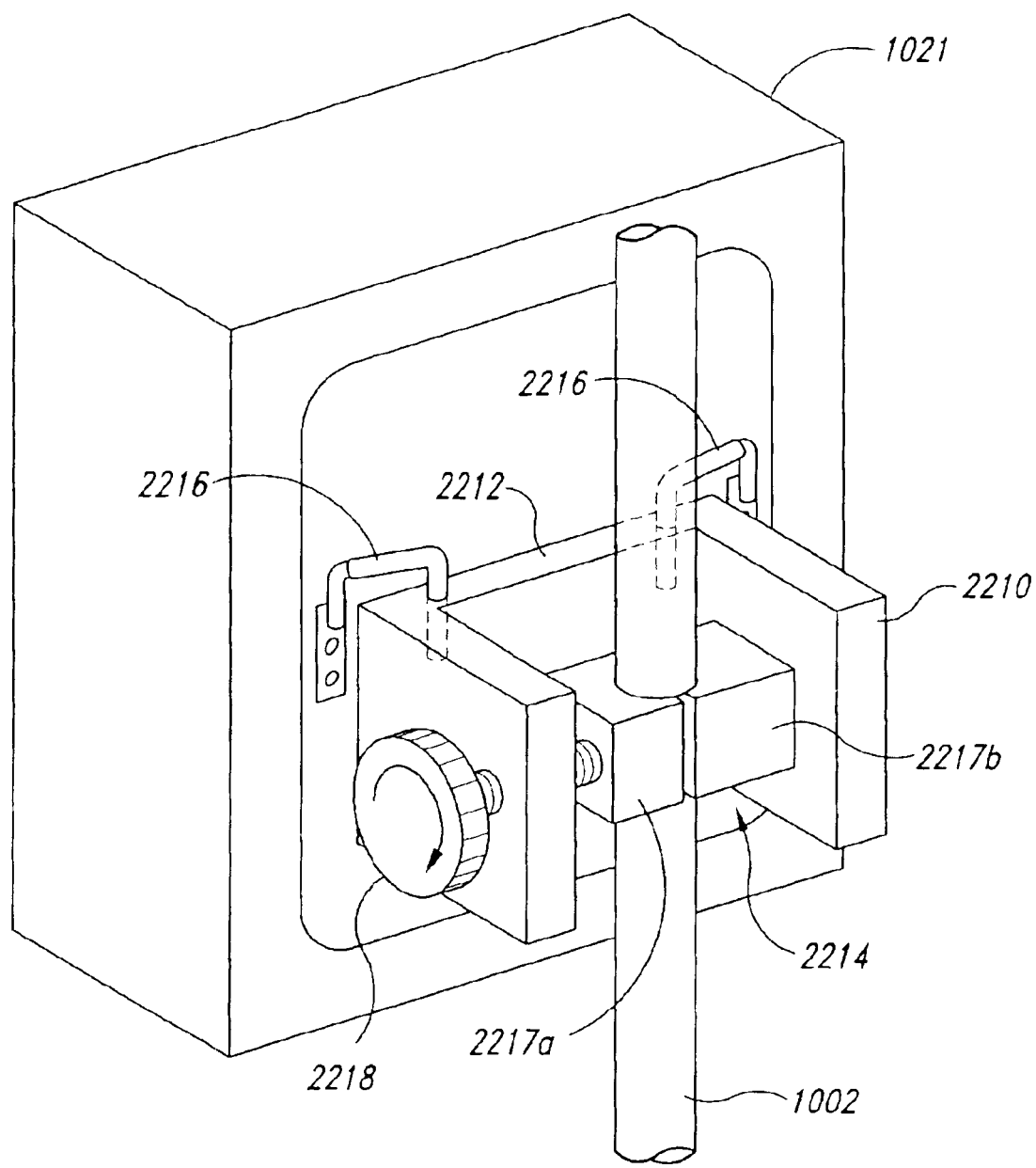
FIG. 22 is an enlarged rear isometric view of the heating pad control unit of FIG. 10 illustrating an attachment device configured in accordance with an embodiment of the invention.

FIG. 22 is an enlarged rear isometric view of the heating pad control unit 1021 of FIG. 10 illustrating an attachment device 2210 configured in accordance with an embodiment of the invention. In one aspect of this embodiment, the attachment device 2210 can include a base portion 2212 and a clamp portion 2214. The base portion 2212 can be releasably attached to the control unit 1021 by, for example, two hooks 2216 extendable outwardly from the control unit 1021. The clamp portion 2214 can include a first v-block 2217a operably connected to a rotatable adjustment knob 2218, and a stationary second v-block 2217b. In another aspect of this embodiment, the control unit 1021 can be releasably attached to the IV pole 1002 by rotating the adjustment knob 2218 to clamp the IV pole 1002 between the first v-block 2217a and the second v-block 2217b.

As will be appreciated by those of ordinary skill in the relevant art, the attachment device 2210 described above with reference to FIG. 22 illustrates but one possible attachment device that can be used to releasably attach the control unit 1021 to a typical OR structure, such as the IV pole 1002. Accordingly, in other embodiments, the control unit 1021 can be releasably attached to IV poles and other structures using other attachment devices. For example, in one embodiment, the control unit 1021 can include hooks that allow it to be releasably suspended from the edge of an OR table.

One skilled in the relevant art will appreciate that embodiments of the invention can be used in various environments other than the medical applications described above. For example, in one other environment, aspects of the invention can be utilized in a home setting to provide personal warmth while sleeping in a particular position. For example, if a person needs to sleep in a particular position for recuperation from a medical procedure, or for other reasons, one or more of the devices described above can be used to maintain such a position while providing sufficient warmth to the person. Further, it is expected that various embodiments of the invention described above can be used in pediatric settings for newborn and young children to provide warmth during sleep. In yet other applications, it is expected that various embodiments of the devices described above can be utilized during transport of persons in need of medical aid. Such transport may include, for example, ambulance transport in civilian and military settings.

Unless the context clearly requires otherwise, throughout the foregoing description and the following example, the words "comprise," "comprising," and the like are to be construed in an inclusive sense as opposed to an exclusive or exhaustive sense; that is to say, in the sense of "including, but not limited to." Words using the singular or plural number also include the plural or singular number, respectively. Additionally, the words "herein," "above," "below" and words of similar import, when used in this application, shall refer to this application as a whole and not to any particular portions of this application.

The foregoing description of embodiments of the invention is not intended to be exhaustive or to limit the invention to the precise forms disclosed. While specific embodiments of, and examples for, the inventions are described herein for illustrative purposes, various equivalent modifications are possible within the scope of the invention, as those skilled in the relevant art will recognize. For example, while various embodiments of patient positioning/warming devices are described above utilizing one or more types of foam adjacent to a heating element, in other embodiments, other materials in addition to, or in place of, foam can be used to sandwich or otherwise enclose the heating element. Further, while specific types of heating elements are described above for purposes of illustration, in other embodiments, it is expected that various other types of heating elements can be used.

All of the patent applications cited herein are incorporated by reference in their entireties. Accordingly, aspects of the invention disclosed herein can be modified, if necessary, to employ or incorporate the systems, functions and concepts of the cited patent applications to provide yet further embodiments of the inventions. These and other changes can be made to the invention in light of the detailed description.

From the foregoing, it will be appreciated that specific embodiments of the invention have been described herein for purposes of illustration but that various modifications may be made without deviating from the spirit and scope of the invention. Accordingly, the invention is not limited except as by the appended claims.

We claim:

1. A personal warming device usable to warm a patient undergoing an x-ray examination in an x-ray field, the personal warming device comprising:
   a patient support portion configured to support at least a portion of the patient in the x-ray field;
   a heating element positioned at least proximate to the patient support portion, the heating element configured to generate heat to warm the patient when the patient is positioned at least partially on the patient support portion;
   a temperature sensing device positioned at least proximate to the heating element, wherein the temperature sensing device is at least generally transparent to x-rays, and wherein the temperature sensing device is configured to change a characteristic of a light signal passing through it when it is heated to a predetermined temperature;
   a first fiber optic tubes operably coupled to the temperature sensing device; and
   a second fiber optic tube operably coupled to the temperature sensing device, wherein the first fiber optic tube is configured to transmit the light signal to the temperature sensing device, and wherein the second fiber optic tube is configured to transmit the light signal away from the temperature sensing device.

2. The personal warming device of claim 1 wherein the patient support portion includes a compressible foam portion that at least generally overlays the heating element, and wherein the compressible foam portion is positioned at least generally between the temperature sensing device and the heating element.

3. The personal warming device of claim 1 wherein the heating element includes conductive ink disposed on a flexible substrate, and wherein the heating element is configured to generate heat by conducting electrical current through at least a portion of the conductive ink.

4. The personal warming device of claim 1 wherein the heating element includes conductive non-metallic ink disposed on a flexible substrate, and wherein the heating element is configured to generate heat by conducting electrical current through at least a portion of the conductive non-metallic ink.

5. The personal warming device of claim 1 wherein the heating element includes carbon ink disposed on a flexible substrate, and wherein the heating element is configured to generate heat by conducting electrical current through at least a portion of the carbon ink.

6. The personal warming device of claim 1 wherein the patient support portion includes a first foam pad disposed adjacent to a first surface of the heating element, and further comprising a second foam pad disposed adjacent to a second surface of the heating element opposite the first surface of the heating element.

7. The personal warming device of claim 1 wherein the heating element includes at least a first layer of polyester film carrying a conductive ink, and wherein the heating element is configured to generate heat by conducting electrical current through at least a portion of the conductive ink.

8. The personal warming device of claim 1 wherein the heating element includes a first conductive lead spaced apart from a second conductive lead to define a space therebetween, wherein the heating element further includes conductive ink extending at least partially between the first and second conductive leads, and wherein the heating element is configured to generate heat by conducting electrical current through at least a portion of the conductive ink.

9. The personal warming device of claim 1 wherein the heating element includes first and second conductive leads carried by at least one layer of polyester film, wherein the first conductive lead is spaced apart from the second conductive lead to define a space therebetween, wherein the heating element further includes conductive ink carried by the polyester film and extending at least partially between the first and second conductive leads, and wherein the heating element is configured to generate heat by conducting electrical current through at least a portion of the conductive ink.

10. The personal warming device of claim 1 wherein the patient support portion includes a first pad portion, and further comprising a second pad portion, wherein the heating element and the temperature sensing device are at least generally sandwiched between the first and second pad portions.

11. The personal warming device of claim 1 wherein the temperature sensing device is operatively connected to the heating element via a temperature control circuit, and wherein the temperature control circuit is configured to shut off power to the heating element if the temperature of the heating element exceeds a threshold temperature as sensed by the temperature sensing device.

12. The personal warming device of claim 1 wherein the temperature sensing device is configured to be operatively connected to a display device configured to display a temperature of the heating element.

13. A personal warming device usable to warm a patient undergoing an x-ray examination in an x-ray field, the personal warming device comprising:
a heating element configured to generate heat to warm the patient
a first foam pad disposed adjacent to a first surface of the heating element;
a second foam pad disposed adjacent to a second surface of the heating element opposite the first surface of the heating element;
a carbon fiber sleeve positioned between the first and second foam pads and at least partially enclosing the heating element; and
a temperature sensing device positioned at least proximate to the heating element and configured to respond to changes in temperature of the heating element, wherein the temperature sensing device is at least generally transparent to x-rays.

14. A personal warming device usable to warm a patient undergoing an x-ray examination in an x-ray field, the personal warming device comprising:
a patient support portion configured to support at least a portion of the patient in the x-ray field;
a heating element positioned at least proximate to the patient support portion, the heating element configured to generate heat to warm the patient when the patient is positioned at least partially on the patient support portion;
a first radiolucent temperature sensing device positioned at least proximate to the heating element and configured to respond to changes in temperature of the heating element, wherein the first radiolucent temperature sensing device is operatively connected to the heating element via a first temperature control circuit, wherein the first temperature control circuit is configured to shut off power to the heating element if the temperature of the heating element exceeds a first threshold temperature as sensed by the first radiolucent temperature sensing device; and
a second radiolucent temperature sensing device operatively connected to the heating element via a second temperature control circuit, wherein the second temperature control circuit is configured to shut off power to the heating element if the temperature of the heating element exceeds a second threshold temperature as sensed by the second radiolucent temperature sensing device.

15. A personal warming device comprising:
a patient support portion configured to support at leat part of person;
a heating element positioned at least proximate to the patient support portion, the heating element configured to generate heat to warm the person when the person is positioned at least partially on the patient support portion;
an optical temperature sensing device positioned at least proximate to the heating element and configured to respond to changes in temperature of the heating element, wherein the optical temperature sensing device is at least generally transparent to x-rays, and;
at least one fiber optic cable operatively coupled to the optical temperature sensing device to transmit temperature information from the optical temperature sensing device.

16. The personal warming device of claim 15 wherein the patient support portion includes foam material.

17. The personal warming device of claim 15 wherein the patient support portion includes a plurality of individual foam particles.

18. The personal warming device of claim 15 wherein the patient support portion includes a viscoelastic foam pad at least generally overlaying the heating element.

19. The personal warming device of claim 15 wherein the patient support portion includes a contoured foam portion configured to support at least a portion of the person's body in an elevated position.

20. The personal warming device of claim 15 wherein the optical temperature sensing device includes a thermally responsive device configured to change a characteristic of a light signal passing through it when it is heated to a predetermined temperature.

21. The personal warming device of claim 15 wherein the optical temperature sensing device includes a thermal chromatic liquid crystal.

22. The personal warming device of claim 15 wherein the heating element includes conductive ink disposed on a flexible substrate, and wherein the heating element is configured to generate heat by conducting electrical current through at least a portion of the conductive ink.

23. The personal warming device of claim 15 wherein the heating element includes carbon ink disposed on a flexible substrate, and wherein the heating element is configured to generate heat by conducting electrical current through at least a portion of the carbon ink.

* * * * *

UNITED STATES PATENT AND TRADEMARK OFFICE
CERTIFICATE OF CORRECTION

PATENT NO. : 6,933,469 B2
DATED : August 23, 2005
INVENTOR(S) : Ellis et al.

It is certified that error appears in the above-identified patent and that said Letters Patent is hereby corrected as shown below:

Column 28,
Line 57, "tubes" should be -- tube --;

Column 30,
Line 10, "sufface" should be -- surface --;
Line 51, "leat" should be -- least --.

Signed and Sealed this

Twenty-fifth Day of April, 2006

JON W. DUDAS
*Director of the United States Patent and Trademark Office*

UNITED STATES PATENT AND TRADEMARK OFFICE
CERTIFICATE OF CORRECTION

PATENT NO.         : 6,933,469 B2
APPLICATION NO. : 10/419705
DATED                 : August 23, 2005
INVENTOR(S)       : Ellis et al.

It is certified that error appears in the above-identified patent and that said Letters Patent is hereby corrected as shown below:

<u>Title Page, ITEM (60):</u>  COL 1
Line 2, delete "and",
Line 3, after "Apr. 20, 2002" and before the period, add --and provisional application No. 60/212,380, filed June 14, 2000--.

Signed and Sealed this

Fifth Day of September, 2006

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 6,933,469 B2 |
| APPLICATION NO. | : 10/419705 |
| DATED | : August 23, 2005 |
| INVENTOR(S) | : Ellis et al. |

Page 1 of 1

It is certified that error appears in the above-identified patent and that said Letters Patent is hereby corrected as shown below:

<u>Column 1</u>
Line 12, after "in its entirety by reference" and before the period, please insert --, and which claims the benefit of U.S. Provisional Patent Application No. 60/212,380, filed June 14, 2000--.

Signed and Sealed this

Twelfth Day of December, 2006

JON W. DUDAS
*Director of the United States Patent and Trademark Office*